(12) United States Patent
Kelly

(10) Patent No.: US 10,751,214 B2
(45) Date of Patent: Aug. 25, 2020

(54) FLUID DISPENSER

(76) Inventor: Nigel Kelly, Rye Brook, NY (US)

( * ) Notice: Subject to any disclaimer, the term of this patent is extended or adjusted under 35 U.S.C. 154(b) by 521 days.

(21) Appl. No.: 14/118,353

(22) PCT Filed: May 18, 2012

(86) PCT No.: PCT/US2012/038564
§ 371 (c)(1),
(2), (4) Date: Feb. 24, 2014

(87) PCT Pub. No.: WO2012/159028
PCT Pub. Date: Nov. 22, 2012

(65) Prior Publication Data
US 2014/0213989 A1  Jul. 31, 2014

Related U.S. Application Data

(60) Provisional application No. 61/487,349, filed on May 18, 2011.

(51) Int. Cl.
| | | |
|---|---|---|
| *A61M 35/00* | (2006.01) | |
| *A61F 9/00* | (2006.01) | |
| *G01F 11/12* | (2006.01) | |

(52) U.S. Cl.
CPC .......... *A61F 9/0008* (2013.01); *A61F 9/0026* (2013.01); *G01F 11/125* (2013.01)

(58) Field of Classification Search
CPC ..... A61F 9/0008; A61F 9/0026; G01F 11/125
USPC ......................................................... 604/296
See application file for complete search history.

(56) References Cited

U.S. PATENT DOCUMENTS

| | | | | |
|---|---|---|---|---|
| 5,025,957 A | * | 6/1991 | Ranalletta | A61F 9/0008 222/189.09 |
| 2005/0053501 A1 | | 3/2005 | Akahori | |
| 2010/0022971 A1 | | 1/2010 | Marx | |
| 2010/0286633 A1 | * | 11/2010 | Marx | A61F 9/0026 604/296 |
| 2011/0056990 A1 | * | 3/2011 | Proper | A47K 5/1207 222/181.3 |

FOREIGN PATENT DOCUMENTS

| | | |
|---|---|---|
| EP | 1434037 A2 | 6/2004 |
| GB | 2437616 A | 10/2007 |
| JP | 45029510 A | 1/1967 |

(Continued)

*Primary Examiner* — Andrew J Mensh
(74) *Attorney, Agent, or Firm* — Michael Pettit

(57) ABSTRACT

The current invention discloses a fluid dispenser especially suitable for ophthalmic treatments and delivering of ophthalmic agents such as eye drops. The fluid dispenser incorporates a tube made from compliant materials as the key dosing component. A first point and a second point on the tube may be acted upon by folding the tube or by external elements, making the segment between the first point and the second point a squeezing section that houses a dosing chamber. The squeezing section may be pressed by an anvil or other structures, pressurizing the fluid contained in the dosing chamber so that once the tube is released on one point, the fluid in the dosing chamber is discharged. With each dosing process, a single dose of the fluid is discharged. In addition, the fluid dispenser is capable of delivering a series of doses of the fluid by repeating the dosing process.

18 Claims, 35 Drawing Sheets

(56) References Cited

FOREIGN PATENT DOCUMENTS

| RU | 2004325 C1 | 12/1993 |
|---|---|---|
| SU | 1046618 A | 10/1983 |
| WO | 2011/134929 A2 | 11/2011 |

* cited by examiner

1

FLUID DISPENSER

CLAIM OF PRIORITY

This application claims the priority of U.S. Provisional Application No. 61/487,349 filed on May 18, 2011, the contents of which are fully incorporated herein by reference.

FIELD OF THE INVENTION

The current invention relates to a fluid dispenser. More particularly, the current invention relates to a miniature dispensing device for delivering eye drops or ear drops in small doses. The same dispenser design may also be scaled-up to deliver much larger doses.

BACKGROUND OF THE INVENTION

This patent application fully incorporates by reference the contents of U.S. Ser. No. 61/487,349 with the title "Indexable Fluid Dispenser" filed on May 18, 2011, by the same inventor.

It is common practice to prescribe eye drops for ophthalmic treatments. Consequently, it is desirable to develop apparatus and devices that may help the application of ophthalmic fluids. Furthermore, it is preferred that the fluids are delivered in small doses such as approximately 5 to 50 micro-liters. Moreover, the ophthalmic fluids are preferably dispensed in small droplets that avoid making noticeable impact on the eye.

To ensure that the fluids are delivered properly, a number of dispensers have been developed. However, most of these dispensers have shortcomings such as frequent wastage and high-impact delivery. In addition, some of the existing dispensers have complicated structures that require precision injection molding and complex assembly, making the device more costly to manufacture.

The current invention adopts a number of unique designs to address the problems presented by the other apparatus and devices, ensuring that ophthalmic fluids are properly delivered.

In summary, other fluid dispensing devices are known in the art, but their structures are distinctively different from the current invention. Moreover, the other inventions fail to address all of the problems solved by the invention described herein. A series of embodiments of this invention are illustrated in the accompanying drawings and will be described in more detail herein below.

SUMMARY OF THE INVENTION

The current invention discloses a fluid dispenser for adminstratering a fluid, comprising: a dispenser case; a reservoir suitable for holding a plurality of doses of the fluid; a tube enclosed in the dispenser case, the tube having a first point, a second point, an inlet end and an outlet end, the inlet end being disposed in the reservoir, the outlet end being connected to an outlet orifice, wherein the tube is made from compliant materials and a segment of the tube between the first point and the second point is a squeezing section housing a dosing chamber; and an actuating assembly, which when actuated presses against the squeezing section, causing a dose of a fluid housed in the dosing chamber to be dispensed.

The fluid dispenser draws from the reservoir in order to initially fill the internal volume of a single length of tube. The fluid is held in the tube, prior to its release from the dispenser. The internal volume of the tube acts as a buffer between the supply of fluid from the reservoir and expulsion of a dose of liquid from the outlet orifice of the dispenser. The inlet end of the tube draws fluids contained in the reservoir. The fluid dispensed may be any fluid or liquid. The fluid may be a pharmaceutical formulation, solution, gel, or suspension. The fluid may be delivered to the eye, ear, or any other targets. A finite number of operations of the dispenser are then required to fill the tube along its length. However, the exact dose that exits the dispenser for delivery to the target is not instantaneously provided by the reservoir. Instead, a segment of the tube is mechanically sequestered to form a squeezing section so that the segment may emits one dose of the fluid to be dispensed when the segment is pressed. The dispenser is designed so that when a dose of the fluid is discharged, the squeezing section is refilled and the dispenser is capable of another discharge for the same dose.

In the current invention the operating force required to ensure complete dosing is first accumulated by an actuating assembly having a spring, or springs, or other operating mechanism capable of creating innate mechanical tension within the dispenser. The accumulated force generated by the actuating assembly is later released by a trigger mechanism, which is also considered part of the actuating assembly, driving the fluid contained in the dosing chamber to be discharged. The actuating assembly may include a push button, pressing of which starts and continues the dosing process. The various alternative trigger mechanisms do not buckle under a given force applied by the operator but, rather, are released under the 'permission' of a tripping-structure reaching a given position of actuation in concert with the downward motion of the push button.

The current invention relies on the sequenced manipulation of the squeezing section, which is between the first point and a second point on the tube. Such a design dictates that discrete doses can be released from the outlet orifice as one single discharge of liquid. A segment of the tube is, essentially 'cordoned-off' (or 'shut-off') by the external application of various devices that press or fold the tube in the first point and the second point—thereby defining part of the tube as the squeezing section that houses the dosing chamber, which contains at least one dose of the fluid. Further external manipulation of the tube on the squeezing section generates an increase in pressure within the dosing chamber. Subsequent release of one of the 'shut-off' points allows the liquid to move out of the dosing chamber and along the tube and, thereafter, to be released from the outlet orifice.

Upon release from the outlet orifice, the fluid dosage stream forms itself into a collection of droplets as it moves through the air (as an inevitable consequence of surface tension effects—which cause streams to break into droplets). Preferably, the dose is approximately between 5 to 50 micro-liters. The entire discharge (dosage) then moves under the assistance of gravity to arrive at a fixed position at a known distance in front of, and below, the outlet orifice, if the outlet orifice is leveled. Alternatively, the outlet orifice may be inclined upward at an angle of between 1 to 30 degrees (typically 15 degrees) from the horizontal plane, so that the descending arc of the dosage path (as the dosage path is acted upon by forward momentum and gravity) may bring the dosage to a known and predictable position horizontal to the outlet orifice at a set distance (generally between 1 to 2 inches) in front of, and level with, the outlet orifice. The dispenser may be also be leaned forward to deliver a dose to a person whose eye is directly below the dispenser, as is typical with the use of dropper bottles The current invention provides for the dose of fluid to be expelled at a flow rate sufficiently low to limit the break-up of the dose into only a few closely grouped droplets. It is a primary objective of this invention to deliver doses of the fluid, such as eye drops, substantially in a manner that is assisted by gravity to follow a known, and predictable, trajectory.

Various targeting/alignment aids may be provided to point toward the position in space, out in front of the outlet orifice, where the dose will arrive at given operating range. Since the dosage may emanate along a gravity-assisted arc, and a targeting structure may be provided which are predictive of this arc, a targeting structure may allow the dispenser to be accurately directed to ensure successful administration of the dose into a target, such as the recipient's eye. The targeting structure is of limited use by a person who is self-administering eye drops, since the dispenser alignment aid is too close to the eye to allow for sharp focusing. However, the alignment aid is of significant practical use by a person who is placing drops in the eye of another person— such as where a physician uses the dispenser to place drops in the eye of a patient.

The preferred process for making the fluid dispenser of the current invention is by means of injection molding. However, since there are no critical sealing surfaces between injection molded parts in the current invention, the use of dissimilar families of plastics to achieve low coefficients of sliding friction is not a requirement or limitation. A wide range of materials, including thermoplastics may, therefore, be used, including: acrylics, co-polymers, polypropylene, and most other families of plastic resin.

The fluid dispenser disclosed by the current invention may be used for various purposes. Preferably, the current fluid dispenser is an ophthalmic dispenser used for administratering eye drops. Nevertheless, the current fluid dispenser may be used for the application of other materials. For example, the dispenser may include an extended nozzle or external tube to enable the device to be used to deliver an ear medicine or an oral vaccine. The current dispenser may also be scaled up for the delivery of large doses of fluid.

The actuating assembly, or pump head, of the current invention may vary in its design and two basic structures are disclosed herein. However, it should be noted that variations of the actuating assembly, as well as other parts of the fluid dispenser, are in the purview of the current invention as long as the central concept remains the same. Similarly, the reservoir for containing the fluid to be dispensed may have different designs, of which there are several variants shown, including where the reservoir is integral of, or separable from the dispenser case.

The fluid dispenser may also include a shield for obscuring the user's operating finger from the view of the person receiving the drops. This design prevents the recipient from closing his/her eye in anticipation of receiving eye drops.

The above features may be combined in any combination to construct alternative configurations of the dispenser. These features of the invention will be better understood through the detailed description and accompanying drawings.

In general, the present invention succeeds in conferring the following, and others not mentioned, desirable and useful benefits and objectives.

It is an object of the present invention to provide a fluid dispenser that may be used to deliver ophthalmic fluids such as eye drops.

It is an object of the present invention to provide a fluid dispenser that uses a tube made from compliant materials.

It is an object of the present invention to provide a fluid dispenser that has a section of a tube to be sequestered to define a squeezing section housing a dosing chamber.

It is an object of the present invention to provide a fluid dispenser that has an actuating assembly that acts on the squeezing section to pressurize the dosing chamber.

It is an object of the present invention to provide a fluid dispenser which includes a trigger mechanism that allows discharge of a dose of the fluid from the dosing chamber.

It is an object of the present invention to provide a fluid dispenser that discharges a precise dose of a fluid with each dosing process.

It is an object of the present invention to provide a fluid dispenser that is capable of delivering a series of doses with repetitive dosing processes.

It is an object of the present invention to provide a fluid dispenser that is light and portable.

It is another object of the current invention to provide a fluid dispenser that may be used for different purposes.

It is another object of the current invention to provide a fluid dispenser that may be used for delivery of ear drops.

It is still another object of the current invention to provide a fluid dispenser that is simple in structure and easy to manufacture.

It is yet another object of the current invention to provide a fluid dispenser that discharges a stream of fluid in a trajectory partly determined by gravity.

It is yet another object of the current invention to provide a fluid dispenser that, in use, does not contact a person's eye, the eye lids, the eye lashes, and soft tissues surrounding the eye.

It is yet another object of the current invention to provide a fluid dispenser that is easy to use.

BRIEF DESCRIPTION OF THE DRAWINGS

FIG. 2b shows a view on B B' as indicated in FIG. 2a

FIG. 2c shows a view on C C' as indicated in FIG. 2a

DESCRIPTION OF THE PREFERRED EMBODIMENTS

Figure 1A:
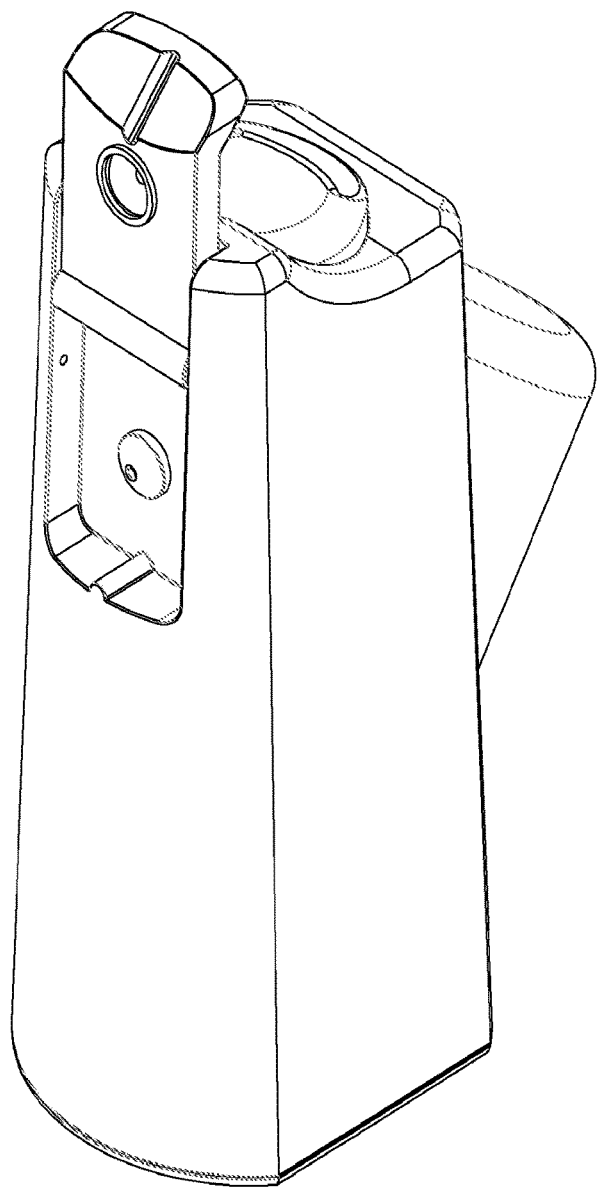
FIG. 1a is a perspective view of a first embodiment of the fluid dispenser in a pre-operated position.

The preferred embodiments of the present invention will now be described with reference to the drawings. Identical elements in the various figures are identified, as far as possible, with the same reference numerals. Reference will now be made in detail to embodiments of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto without deviating from the innovative concepts of the invention.

FIG. 1a is a perspective view of a first preferred embodiment of the fluid dispenser 1, providing a general outlook of the fluid dispenser.

Figure 1B:
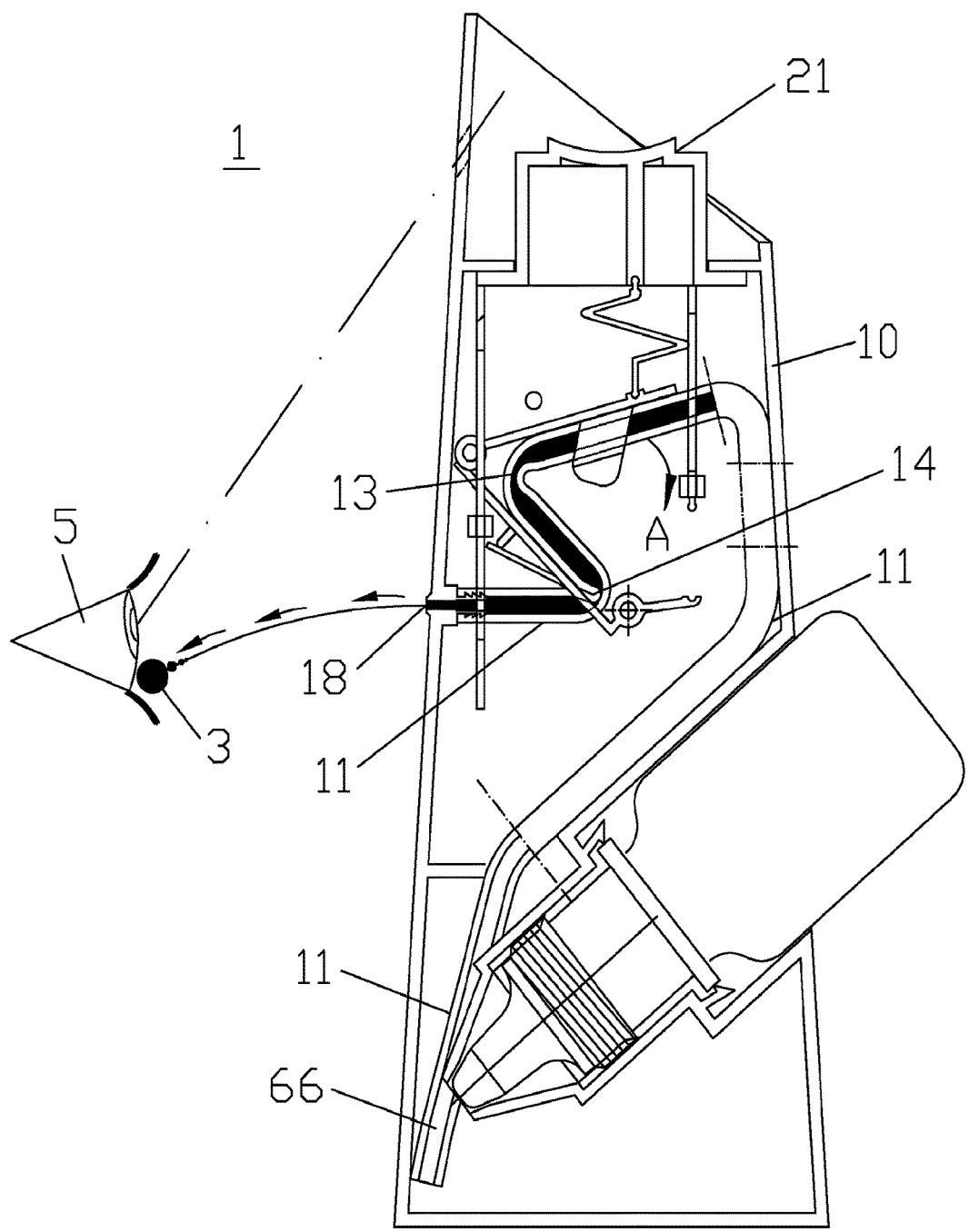
FIG. 1b is a section view of a first preferred embodiment of the fluid dispenser in a pre-operation position.

FIG. 1b is a section view of a first preferred embodiment of the fluid dispenser 1 in a pre-operation position. Shown in FIG. 1b is the fluid dispenser 1 having a dispenser case 10, a tube 11 residing in the dispenser case, and the push button 21 in a resting position. The tube 11 has a bore 66, a first articulating point 13 and a second articulating point 14. The tube 11 may fold at the first articulating point 13 and the second articulating point 14. When the push button 21 is in the rest position—push button 21 not being pressed downward, the tube 11 is not fully folded at the first articulating point 13, allowing the fluid in the rest of the bore 66 to move past the first articulating point 13. However, in the rest position, the tube 11 is folded in a sufficient angle at the second articulating point 14 so that no fluid may flow pass that point. Arrow A indicates the direction through which the tube 11 will articulate during the dosing process when the push button 21 is being pressed downward.

The fluid dispenser 1 may be used for various purposes. The preferred use of the fluid dispenser 1 is to deliver eye drops 3 to an eye 5, as shown in FIG. 1b. The fluid dispenser 1 may be used in an up-right position, and the fluids discharged from the fluid dispenser 1 may be applied in a trajectory with the assistance of gravity. The fluid dispensed may be any fluid or liquid. The fluid may be a pharmaceutical formulation, solution, gel, or suspension. The fluid may be delivered to the eye, ear, or any other targets. The viscosity of the fluid to be dispensed may range between 0.5 centipoise and 2000 centipoise, with a preferred range of 0.8 to 30 centipoise.

The fluid dispenser 1 may be made from any materials that suit the requirements to allow the fluid dispenser 1 to operate properly. The dispenser case 10, which forms a framework enclosure that houses the other components of the fluid dispenser 1, may be made from materials that include but are not limited to metal, wood, and plastics such as but not limited to, polyethylene terephthalate (PET), polyethylene (PE), high-density polyethylene (HDPE), polyvinyl chloride (PVC), polyvinylidene chloride (PVDC), low-density polyethylene (LDPE), polypropylene (PP), polystyrene (PS), high impact polystyrene (HIPS) and polycarbonate (PC), or paperboard coated with a suitable waterproof coating such as, but not limited to, polyethylene, or some combination thereof. The preferred material for the dispenser case 10 is plastic, including but not limited to: acrylics, co-polymers, polypropylene, and most other families of plastic resin. Similarly, the various components of the fluid dispenser 1 may be made from the same or different materials as the dispenser case 10. Some components may have special requirements as to the property of the materials. For example, for the spring members, the materials need to be durable and resilient. For such components, materials are chosen specifically to fit the needs.

Figure 1C:
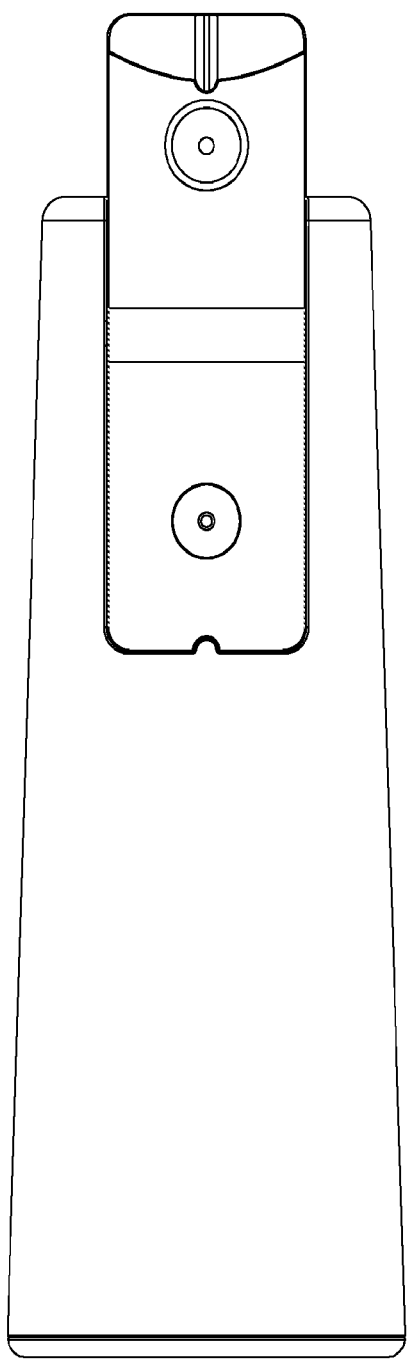
FIG. 1c is a front view of a first embodiment of the fluid dispenser in a pre-operated position.

FIG. 1c is a front view of a first preferred embodiment of the fluid dispenser 1.

Figure 2A:
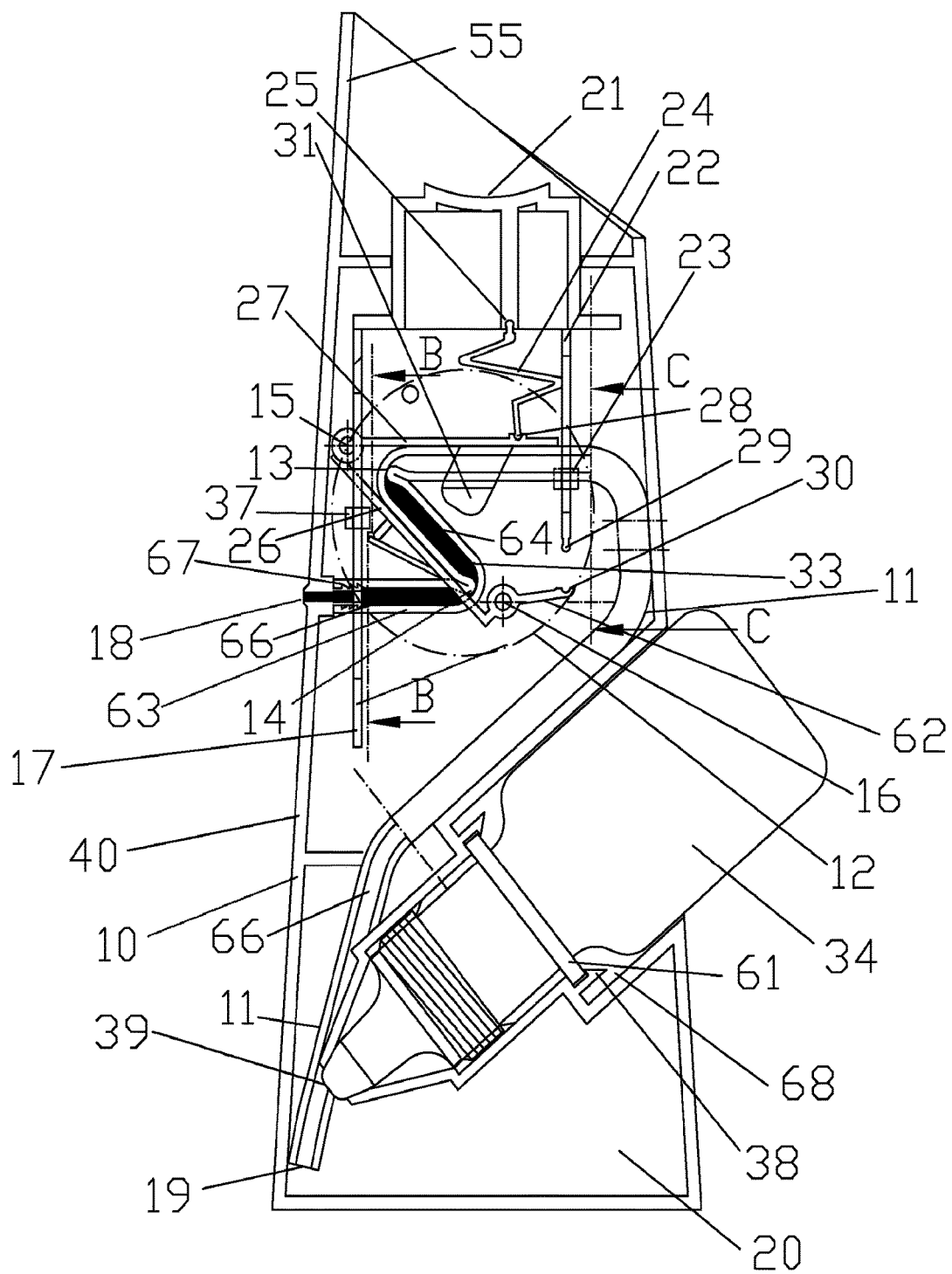
FIG. 2a shows a section view of the first preferred embodiment of the fluid dispenser at the first stage of operation.
Figure 2B:
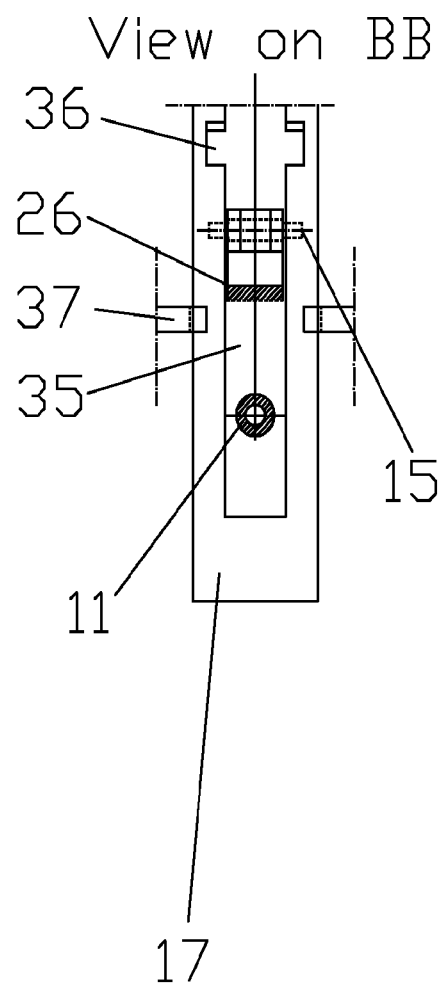
Figure 2C:
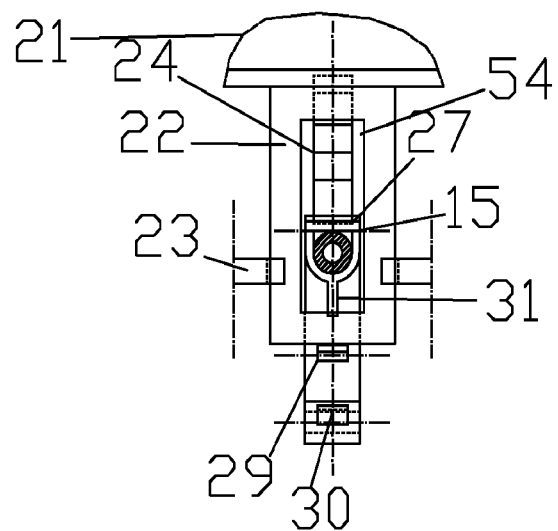

FIG. 2a shows a section view of the first preferred embodiment of the fluid dispenser 1 at the first stage of operation. FIG. 2b shows a view on B B' as indicated in FIG. 2a. FIG. 2c shows a view on C C' as indicated in FIG. 2a. FIG. 2a also serves to illustrate the detailed structures of the first preferred embodiment. Shown in FIG. 2a is the fluid dispenser 1 of the current invention having a tube 11, preferably made of a compliant material that is flexible, easy to deform, and with low stiffness, preferably having a durometer of between 30 and 70 Shore hardness. The tube 11 is preferably bent into a reversed 'Z' form 12. The tube 11 has a bore 66, a fluid inlet end 19 fluidly suspended in a holding tank 20 containing the fluid to be dispensed, and a fluid outlet end 67 connected to an outlet orifice 18 to form the discharge structures of the fluid dispenser 1.

The tube 11 resides in the dispenser case 10 and it is the key structure of the fluid dispenser 1. The tube 11 has a bore 66, which serves as a flowing channel, a storing chamber, and a discharging sub-device for the fluid dispenser 1. The tube 11 is preferably made from compliant material that is flexible and low in stiffness. Such complaint materials including but not limited to rubber and plastics. In FIG. 1 and FIG. 2a, as well as the remaining figures, the tube 11 is shown from partly cut-away and partly closed views. The dark substance shown in the bore 66 of the tube 11 illustrates the fluid to be dispensed.

Also shown in FIG. 2a is a dropper bottle 34 installed into a holding slot 68 in the dispenser case 10 with the dropper bottle 34 having its nozzle 39 still installed. The dropper bottle 34 is retained in the holding slot 68 by claws 38, which snap over the flange 61 of the dropper bottle 34 to prevent it from being removed from the dispenser case 10 once it has been disposed in position. The dropper bottle 34 and the holding tank 20, in combination, may serve as a reservoir that provides the fluid to be discharged from the fluid dispenser 1. With the design shown in FIGS. 1-4, the tube 11 derives the fluid to be dispensed directly from the holding tank 20. The dropper bottle 34, on the other hand, may be squeezed to decant its contents into the holding tank 20, providing extra supply to refill the holding tank 20.

Figure 9:
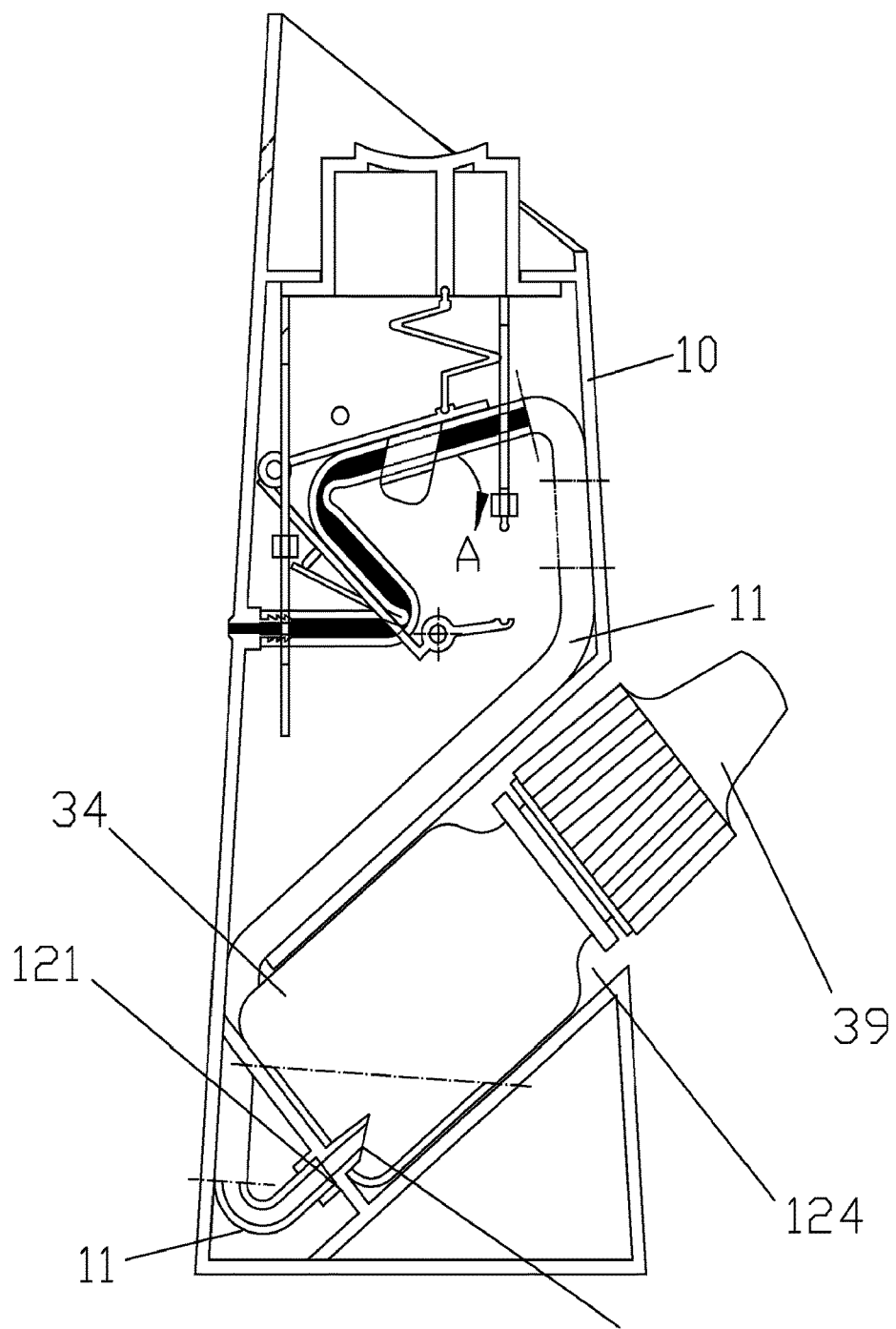
FIG. 9 shows the section view of a fluid dispenser with a conventional dropper bottle, complete with its nozzle, acting as the external reservoir for the fluid to be dispensed.

The dropper bottle 34 is an optional structure for the fluid dispenser 1. Having a dropper bottle 34 ensures plentiful of supply for the fluid dispenser 1. Alternatively, the dispenser case 10 may have no structure to accommodate the dropper bottle 34 or any other refill mechanisms. The fluid dispenser 1 may only include an integral reservoir, as shown in FIGS. 10-14. Such an integral reservoir does not require an extra supply of the fluid to be dispensed. Similarly, the holding tank 20 may be omitted from the design of the fluid dispenser 1 and the dropper bottle 34 or other detachable container may serve as a direct source of the fluid to be dispensed. Such a design is shown in FIG. 9. In general, the structure of the reservoir—the source of the fluid to be dispensed, may vary significantly. As long as the general purpose of providing fluid for the fluid dispenser 1 is satisfied, any specific design is acceptable.

Also shown in FIG. 2a is that the tube 11 folds at the first articulating point 13 and the second articulating point 14, defining a squeezing section 64 between the two articulating points, the squeezing section 64 having a dosing chamber 33, wherein the dosing chamber 33 holds the fluid to be dispensed. Between the fluid outlet end 67 of the tube 11 and the second articulating point 14 there is a discharge section 63.

The fluid dispenser 1 is suitable for discharging a single dose of fluid in each dosing process. The dose discharged in each dosing process may vary according to a series of factors such as but not limited to the dimension of the bore 66, the degree to which the dosing chamber is squeezed, and the distance between the first articulating point 13 and second articulating point 14. Preferably, the dose is between 1 to 100 micro-liters, with the preferred dose to range approximately 5 to 50 micro-liters. Moreover, the fluid dispenser 1 may be scaled up for use in larger discharges such as a water pump. In that case, the dose may be as large as 100 liters. Preferably, with each dosing process, a single dose of the fluid is discharged from the fluid dispenser 1. In addition, the fluid dispenser 1 is capable of delivering a series of doses of the fluid with repetitive dosing processes.

Preferably, the outlet orifice 18 has a slow taper in its bore (in the range of 1 to 5 degrees) to assist in the injection molding process and so as to allow the discharge of the liquid being dispensed to maintain a laminar flow. Since its discharge velocity is low, it requires only a short bore in the outlet orifice 18 to maintain laminar flow—generally a length-to-bore ratio of under 7:1 is acceptable. A 6:1 ratio, or less, is advantageous. This short aspect ratio of length-to-bore renders the manufacture of the outlet orifice 18 easy to injection mold.

FIG. 2a shows the push button 21 and a first spring member 24 attached to the lower portion of the push button 21. Attached to the left lower portion of the push button 21 is a cantilever plate 17, which extends downward. Similarly, attached to the right lower portion of the push button 21 is a push plate 22, which also extends downward. The first spring member 24 is linked to the push button 21 at attachment point 25. The bottom of first spring member 24 is attached to hinge plate 27 at attachment point 28.

FIG. 2a also shows a first hinge-piece 26 and a second hinge-piece 27, wherein the first hinge-piece 26 and the second hinge-piece 27 hold the reversed 'Z' form 12 of the tube 11 in position so that the tube 11 and hinge-pieces move in unison. The first hinge-piece 26 is aligned against the dosing chamber 33 and the second hinge-piece 27 is attached to the first spring member 24. As shown in FIG. 2a, there is a first pivot 16 on the first hinge-piece 26 and a second pivot 15 on the second hinge-piece 27. Moreover, the second hinge-piece 27 has an anvil 31 attached to it. The anvil 31 may articulate with the second hinge-piece 27 and may apply pressure to the squeezing section 64 of the tube 11.

The cantilever plate 17 and the push plate 22 are flat pieces that are illustrated in more detail in FIGS. 2b and 2c. Points B and B' serve as indicators for the viewing of the cantilever plate 17, which is shown in FIG. 2b. Similarly, points C and C' serve as indicators for the viewing of the push plate 22, which is shown in FIG. 2c. As shown in FIG. 2b, the cantilever plate 17 is held in place by two cantilever plate supports 37 and the cantilever plate 17 has a cantilever plate opening 35 with an elongated rectangular shape. The cantilever plate opening 35 has an enlarged portion 36 in the top part of the elongated rectangle. As shown in FIG. 2c, the push plate 22 is held in place by two push plate supports 23 and the push plate 22 has a push plate opening 54.

Referring to FIG. 2a and FIG. 2b, the tube 11, the second pivot 15, and first hinge-piece 26 are located such that they project through the cantilever plate opening 35 in the cantilever plate 17. Cantilever plate 17 extends from the underside of push button 21, and is able to slide vertically. The two cantilever plate supports 37 restrict the path of vertical movement by the cantilever plate 17. The second pivot 15 has a width larger than the width of the cantilever plate opening 35 but smaller than the enlarged portion 36. Similarly, the second hinge-piece 27 and tube 11 pass through the push plate opening 54 on the push plate 22, as shown in FIGS. 2*a* and 2*c*. In addition, the push plate 22 may slide downward when the push button 21 is pressed and the push plate supports 23 restrict the vertical movement of the push plate 22. The cantilever plate supports 37 and the push plate supports 23 are attached to the dispenser case 10.

As shown in FIG. 2*a*, the bottom of push plate 22 has a rounded projection 29. The first hinge piece 26 has a cantilever extension 62 adjacent to pivot 16, the cantilever extension 62 having a rounded trough 30 that matches the form of rounded projection 29 on push plate 22.

The discharge section 63 and the squeezing section 64 of the tube which are held by the hinge-pieces 26 and 27 articulate through an angular range, so that the tube bore 66 at articulation points 13 and 14 are, independently, either partially open—to allow for the fluid to travel through the tube 11, or fully closed—such that the tube bore 66 is fully constricted (or closed-off) to the movement of liquid along the tube bore 66.

FIG. 2*a* shows the fluid dispenser 1 as an initiating stage. The push button 21 is pressed halfway downward and the first spring member 24 is constrained, preparing for a motion to apply pressure to the first hinge-piece 26 and further to the tube 11. At this stage, the tube bore 66 at the first articulating point 13 and second articulating point 14 are closed and the squeezing section 64 is fully sequestered.

FIG. 2*a* also shows an extended shroud 55 which extends around the top of the dispenser case 10 to shield push button 21 from the view of a patient. When the fluid dispenser 1 is used to administer eye drops by a physician to a patient's eye (as shown in FIG. 1), the shroud 55 may prevent the patient from seeing the movement of the physician's finger. Unable to see the physician's finger moving to operate the dispenser, the patient would be less likely to blink in response to such finger movement and thereby interrupt delivery of the dose to their eye.

Figure 3:
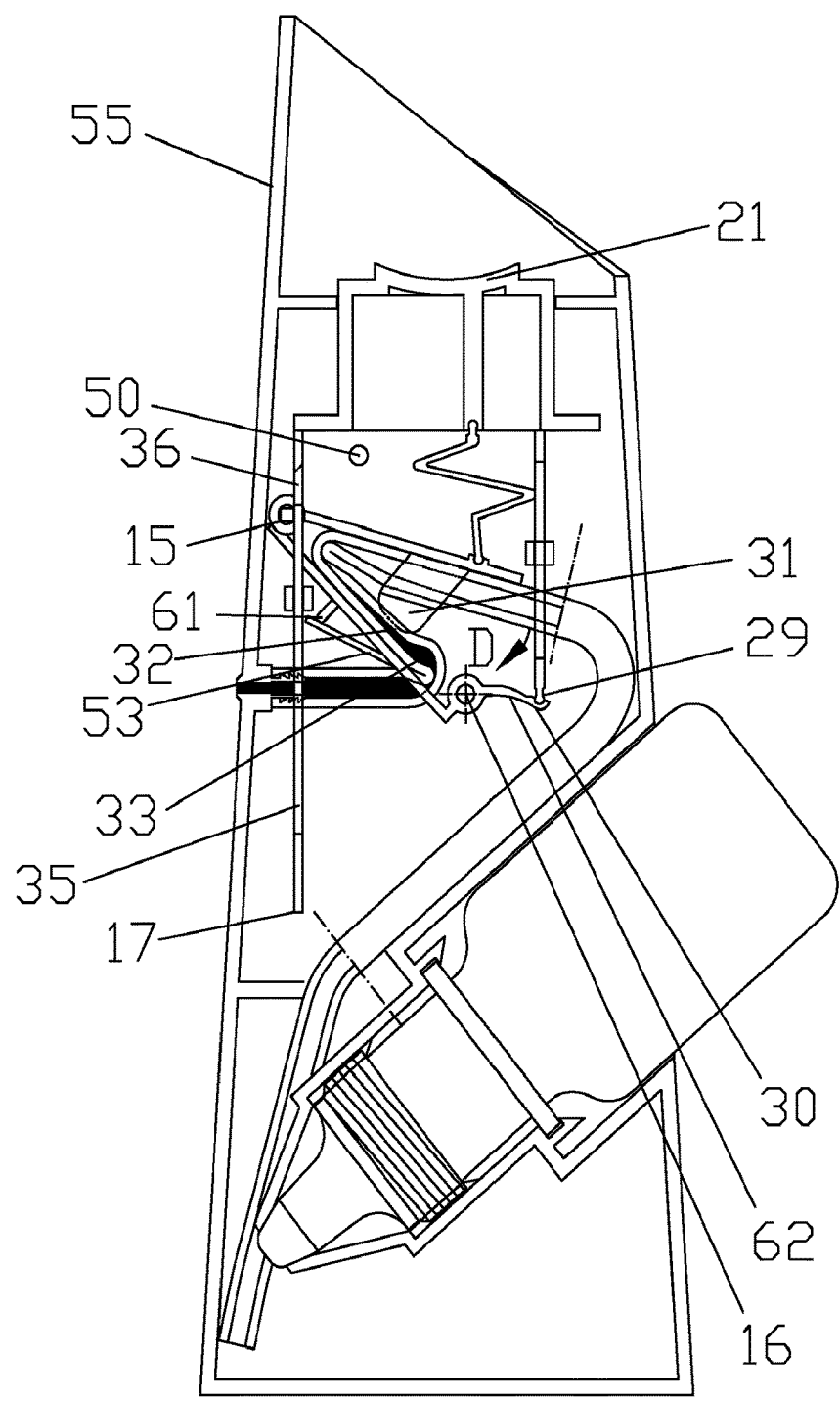
FIG. 3 shows a section view of the first preferred embodiment of the fluid dispenser at the second stage of operation.

FIG. 3 shows a section view of the first preferred embodiment of the fluid dispenser 1 at the second stage of operation. FIG. 3 shows essentially the same elements as FIG. 2*a*, though most of the elements are not marked for clarity purposes. Regarding detailed markings for the specific elements, FIG. 2*a* may be referred to.

Shown in FIG. 3 are the push button 21, the shroud 55, the cantilever plate 17 having a cantilever plate opening with an enlarged portion 36, the push plate 22 having a push plate opening 54 and rounded projection 29, the cantilever extension 62 having a rounded trough 30, the second pivot 15 and the first pivot 16. In addition, FIG. 3 also shows a first stop member 50, a second stop member 61, and a leaf spring 53. The first stop member 50 and the second stop member 61 may be rods or bars that are attached to the dispenser case 10 and they are used to stop the movement of the hinge-pieces 26 and 27. The leaf spring 53 is made from strong and resilient materials such as but not limited to metal or plastic and it is positioned to resist the rotation of the first hinge-piece 26.

Figure 4:
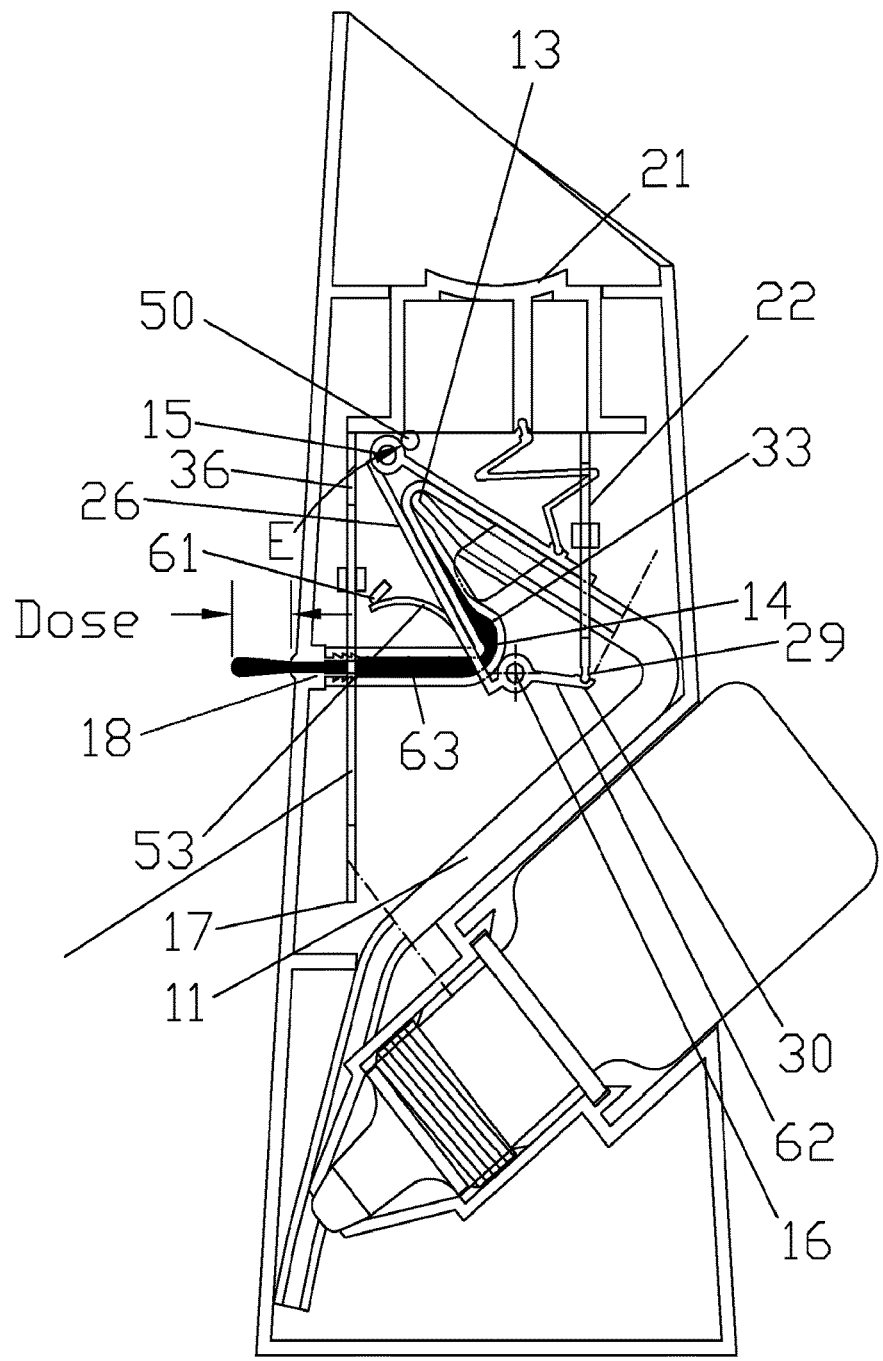
FIG. 4 shows a section view of the first preferred embodiment of the fluid dispenser at the third stage of operation—the discharging stage.

FIG. 4 shows a section view of the first preferred embodiment of the fluid dispenser 1 at the third stage of operation—the discharging stage. FIG. 4 shows essentially the same elements as FIG. 2*a*, though most of the elements are not marked for clarity purposes. Regarding detailed markings for the specific elements, FIG. 2*a* may be referred to.

Shown in FIG. 4 are the push button 21, the cantilever plate 17 having a cantilever plate opening 35 with an enlarged portion 36, the tube 11 having a squeezing section 64, the outlet orifice 18, the first articulating point 13, the second articulating point 14, the push plate 22 having a rounded projection 29, the cantilever extension 62 having a rounded trough 30, the second pivot 15 and the first pivot 16. In addition, FIG. 4 also shows the first stop member 50, the second stop member 61, and the leaf spring 53.

FIGS. 1, 2, 3 and 4, as a group, show the dosing process of the first preferred embodiment the fluid dispenser 1. As shown in FIG. 2*a*, the squeezing section 64 between the first articulating point 13 and the second articulating point 14 of the tube 11 house the dosing chamber 33, wherein the dosing chamber is created when the push button 21 is pressed, which then moves the first spring member 24 downward via attachment point 25. The bottom of first spring member 24 is attached to hinge plate 27 at attachment point 28. The second pivot 15 permits the first articulating point 13 to fully constrict the tube bore 66 and stop the passing of fluid. The bore 66 is also closed at the first articulating point 13 in FIGS. 3 and 4, while in FIG. 1 the tube bore 66 is partially open at the first articulating point 13.

As shown in FIG. 1*b*, in the rest position, tube 11 is constricted at the second articulating point 14. In FIGS. 2 and 3, with the downward movement of the push button 21, the second hinge-piece 27 pushes the tube 11 to articulate at the first articulating point 13. Moreover, the anvil 31 moves with the second hinge-piece 27 and presses the dosing chamber 33 at squeezing point 32, as shown in FIG. 3. The anvil 31 may be an integral part of the second hinge-piece 27 or a close attachment to the second hinge-piece 27. The anvil deforms the outside walls of the tube 11 at squeezing point 32 when both the first articulation point 13 and the second articulation point 14 are folded to the point where the tube bore at both of these points are closed, as shown in FIG. 3. This compression of the squeezing section 64 at squeezing point 32 (indicated in FIG. 3 by Arrow D) generates a rise in the pressure within the dosing chamber 33.

The first spring member 24 drives the articulation of the second hinge-piece 27 with respect to the first hinge-piece 26, and that fixed angular relationship between the hinge-pieces 26 and 27 is maintained by an angular constraint built into the hinge 15 during the remainder of the downward motion of push button 21. The rounded projection 29 comes into contact with the rounded trough 30, bending the cantilever extension 62, as shown in FIG. 3—thus imparting torque to the first hinge-piece 26 around pivot point 16. This torque is resisted by cantilever plate 17, which blocks the articulation of hinge-piece 27 due to the outer ends of pivot 15 being too long to pass through the cantilever plate opening 35.

Referring to FIGS. 3 and 4, push button 21 travels down further, and along with it cantilever plate 17 and push plate 22 also travels downward, until pivot 15 reaches the enlarged portion 36—at which point pivot 15 is able to pass through cantilever plate 17 in the direction of stop 50—acting under the bending moment already exerted in hinge-piece 26 by the bent cantilever extension 62. As shown in FIG. 4, this freedom permitted to hinge-pieces 26 and 27 enables the discharging operation of the pump. As the assembly of hinge-pieces 26 and 27, and tube 11, swing through an upward arc (shown in FIG. 4 by arrow E), the second articulation point 14 opens by the rotation of hinge-pieces 26 and 27 around pivot 16. This allows the pressurized fluid to escape from the dosing chamber 33 via the discharge section 63 and the outlet orifice 18. During this articulation, the hinge-pieces 26 and 27 maintain a fixed angular relationship relative to each other, while the second pivot 15 swings upward toward first stop member 50. Simultaneously with the hinge plates 26 and 27 swinging upward in this manner, the leaf spring 53 bends against the second stop member 61 and thereby offering increasing resistance against the further rotation of the second hinge-piece 27.

Once discharging is complete, and force applied on push button 21 is removed, bent leaf spring 53 reverses the motion of pivot 15 back through the enlarged portion 36 of the cantilever plate opening 35, and cantilever extension 62 returns the second hinge-piece 27 to its rest position. The compression held in the first spring member 24 then enables it to return push-button 21 back to its rest position, as shown in FIG. 1.

Figure 5A:
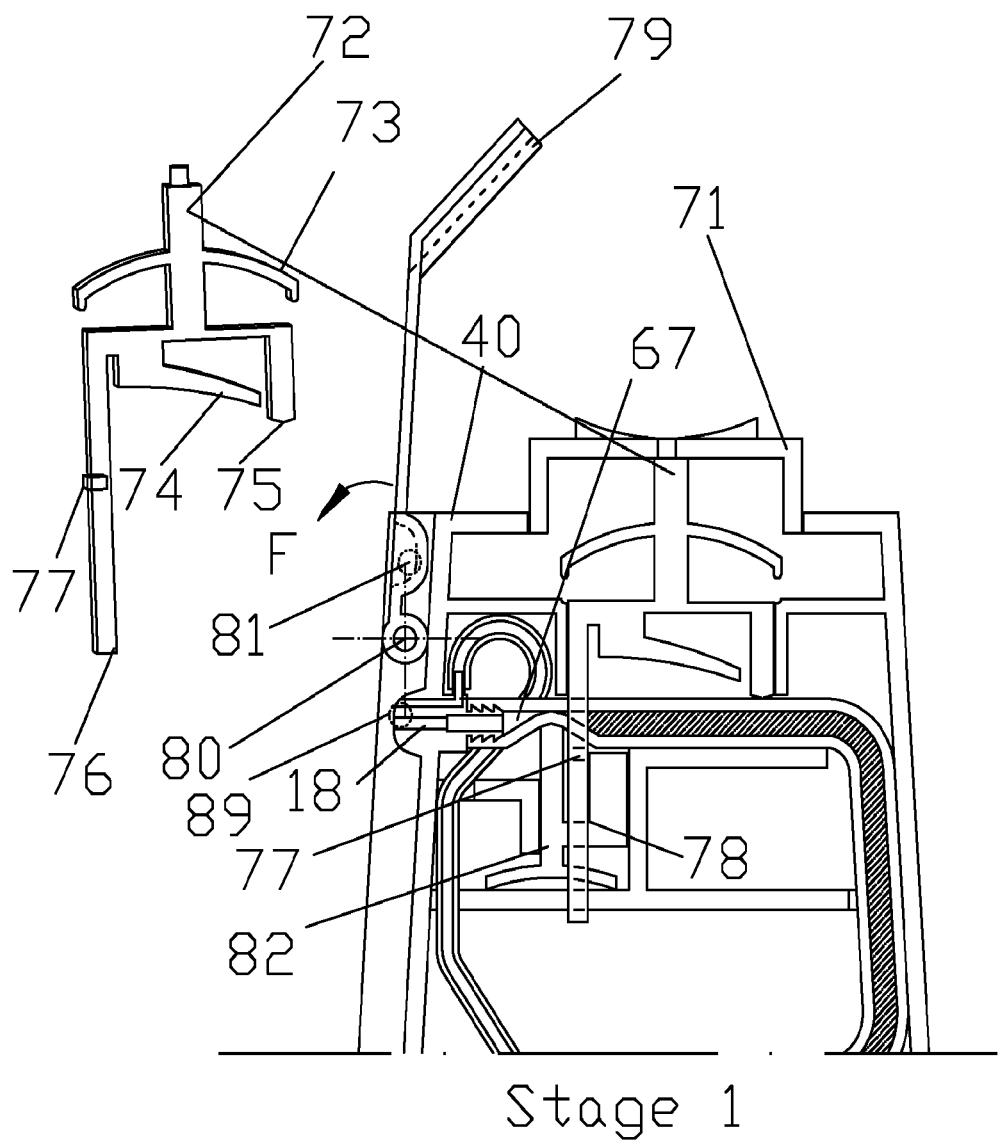
FIG. 5a shows a section view of a second preferred embodiment of the invention, with an alternative pump head design including a flip-closure, showing the first stage of operation.
Figure 5B:
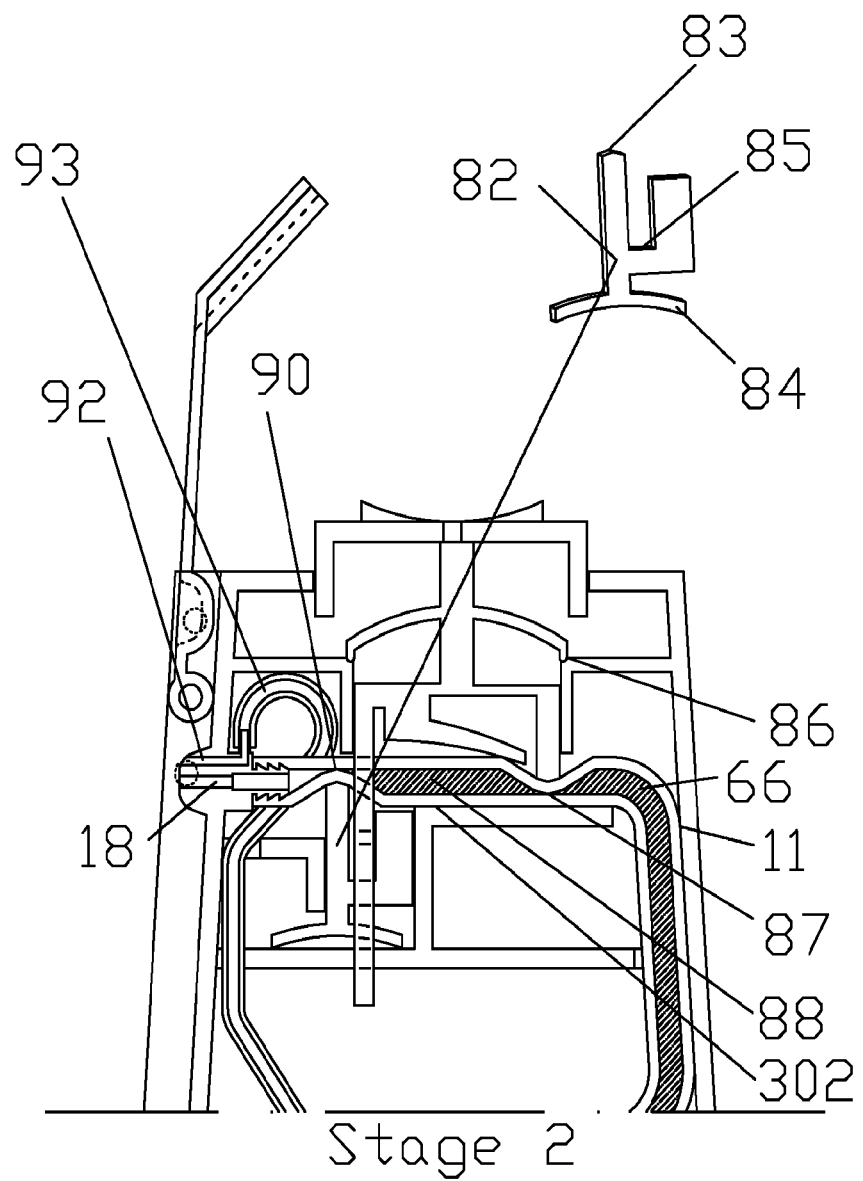
FIG. 5b shows a section view of a second preferred embodiment of the invention, with an alternative pump head design including a flip-closure, showing the second stage of operation.

FIGS. 5a and 5b show a section view of a second preferred embodiment of the invention. The second preferred embodiment shares some similar elements as the first preferred embodiment, such as having a dispenser case 10 and a tube 11 enclosed in the dispenser case 10. However, the arrangement of the tube 11, and correspondingly, the design of the actuating assembly (pump head), are different from the first preferred embodiment. FIGS. 5a and 5b show the second preferred embodiment with an alternative pump head design, and flip-closure/finger guard. The first two stages of pump operation are shown in FIGS. 5a and 5b, respectively.

Shown in FIGS. 5a and 5b is the tube 11 having a bore 66, wherein the tube 11 is preferably made of a compliant material such as plastic or rubber, has a fluid inlet end 19 (not shown in FIG. 5a or 5b) suspended in holding tank 20 (not shown in FIG. 5a or 5b), which contains the fluid to be dispensed, and a fluid outlet end 67 connected to an outlet orifice 18 to form the discharge end of the fluid dispenser 1. The tube 11 in the second preferred embodiment has a horizontal section 302.

FIGS. 5a and 5b also shows a flip closure 79, which may be used to open or close the dispenser. The upright stance of the flip closure 79 corresponds to the "open" position of the dispenser, while the downward stance of the flip closure 79 corresponds to the "close" position of the dispenser. In addition, the flip closure 79, in its upright stance, may also shield the patient's view to the push button 21, serving the same purpose of the extended shroud 55 in the first preferred embodiment. Moreover, the flip closure 79 may have additional structures that may aid the aiming of the discharge from the dispenser (the details of such a design being shown in FIG. 21). The flip closure may pivot within the dispenser case at point 80. In its upright stance, the flip closure 79 is held by upper detent 81. To close the dispenser, the flip closure 79 rotates in the direction of Arrow F until it is held by lower detent 89.

As shown in FIGS. 5a and 5b, one new element of the second preferred embodiment is an anvil plate 82, which is separately illustrated in FIG. 5b for clarity purposes. The anvil plate 82 comprises a first double leaf spring 84, a bottom anvil 83 residing on the first double leaf spring 84 and protruding upwards, and a side branch 85 being parallel to the bottom anvil 83, the side branch 85 being connected perpendicularly to anvil plate 82. The anvil plate 82 is positioned beneath the discharge section 63 of the tube 11. The first double leaf spring 84 has a curved piece with two ends pointing downwards.

Also shown in FIG. 5a is a pressing plate 72, which is separately illustrated in FIG. 5 for clarity purposes. The pressing plate 72 comprises a second double leaf spring 73, a top anvil 75, a sloped shoe 74, a pressing plate leg 76, a pressing plate connector 97, and a pressing plate block 77. The pressing plate 72 is positioned beneath a push button 21 and used as a structure to transfer the forces applied from the push button 21 to the tube 11. The pressing plate leg 76, as shown in FIG. 5, is positioned on the left side of the pressing plate 72 and extends downwards. On the other hand, the top anvil 75 is positioned on the right side of the pressing plate 72. The pressing plate block 77 is attached to the pressing plate leg 76. The second double leaf spring 73 is a curved structure with two ends pointing upwards.

The tube 11 in this embodiment is acted upon by the top anvil 75, the bottom anvil 83, and the sloped shoe 74, in a sequenced pattern. As shown in FIG. 5, stage 1, as liquid travels along the tube 11 toward the outlet orifice 18 it displaces the air in the tube to the point where all the air is expelled from the outlet orifice 18 and only liquid emits from the orifice. The top anvil 75 and the bottom anvil 83 selectively press on the outside of the tube in concert with the downward motion of push button 21 moving within the dispenser case 10, to deform tube 11 so that it is either open to the flow of fluid, or closed to the flow of fluid. In a rest position, as shown in FIG. 5a, the bottom anvil 83 presses against the first pressing point 90 and prevents the fluid in the tube 11 from moving pass the first pressing point 90. The top anvil 75 is not pressed against the tube 11 in a rest position, as shown in FIG. 5a. When the push button 21 is pressed, as in FIG. 5b, the top anvil 75 moves downwards and is pushed against the second pressing point 87 of the tube 11. The first pressing point 90 and the second pressing point 87 define a squeezing section 302 housing a dosing chamber 88, similar to the squeezing section 32 and the dosing chamber 33 in the first preferred embodiment (as shown in FIG. 2a). With the downward movement, the second double leaf springs 73 on the pressing plate 72 engages an interior portion of the dispenser case 10 at a second double leaf spring contacting point 86.

Figure 8:
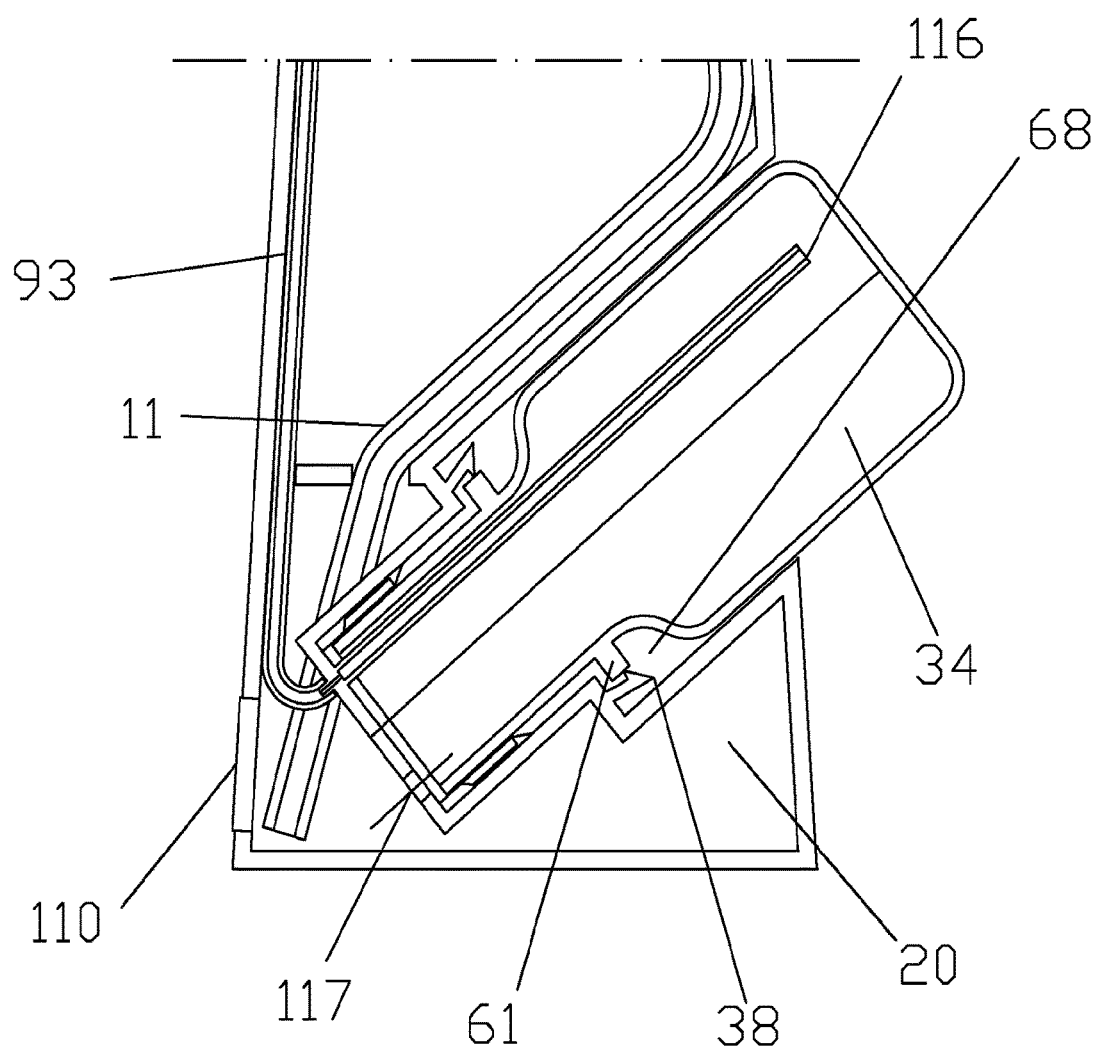
FIG. 8 shows a section view of a part of the fluid dispenser having a conventional dropper bottle attached to the dispenser.
Figure 11:
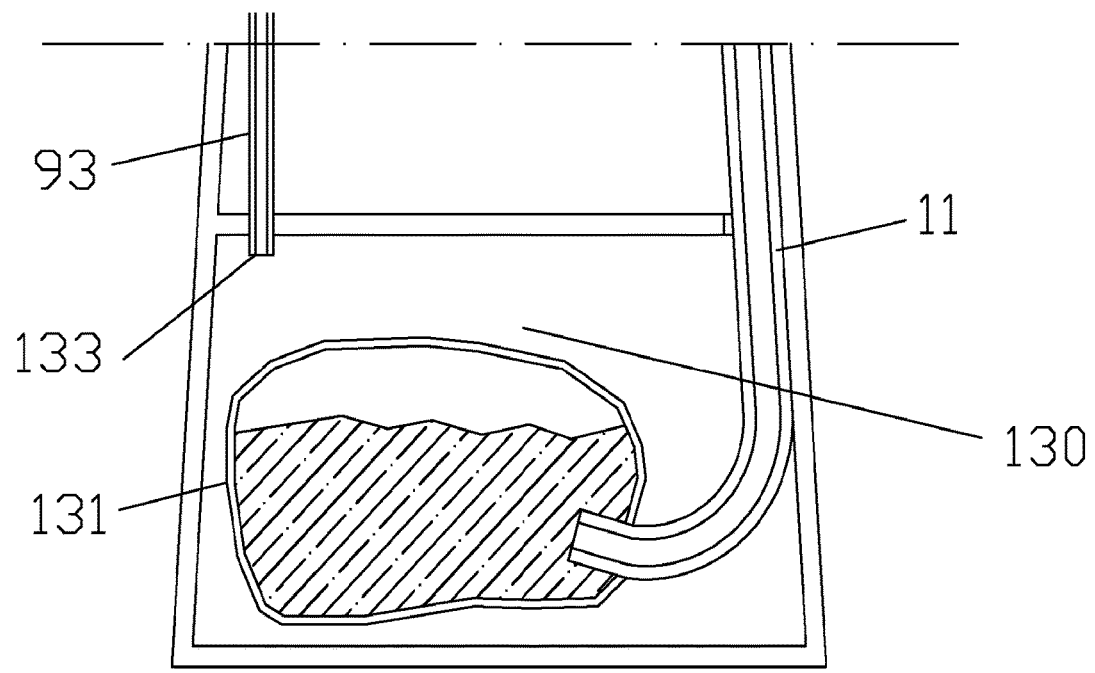
FIG. 11 shows a section view of a second design of an integral reservoir for the fluid dispenser using a collapsible bag.

As shown in FIG. 5b, a vent tube 93 also resides in the dispenser case 10. The vent tube 93 is connected to a vent hole 92 at a first end. The second end of the vent tube 93 may be placed in the reservoir such as the holding tank, as shown in FIGS. 8 and 11. The vent tube 93 and the vent hole 92 serves to provide an air flowing structure to prevent pressure loss in the reservoir. The vent tube is an optional structure. Other designs may replace or supplement it for the function of balancing the pressure in the reservoir.

Figure 6A:
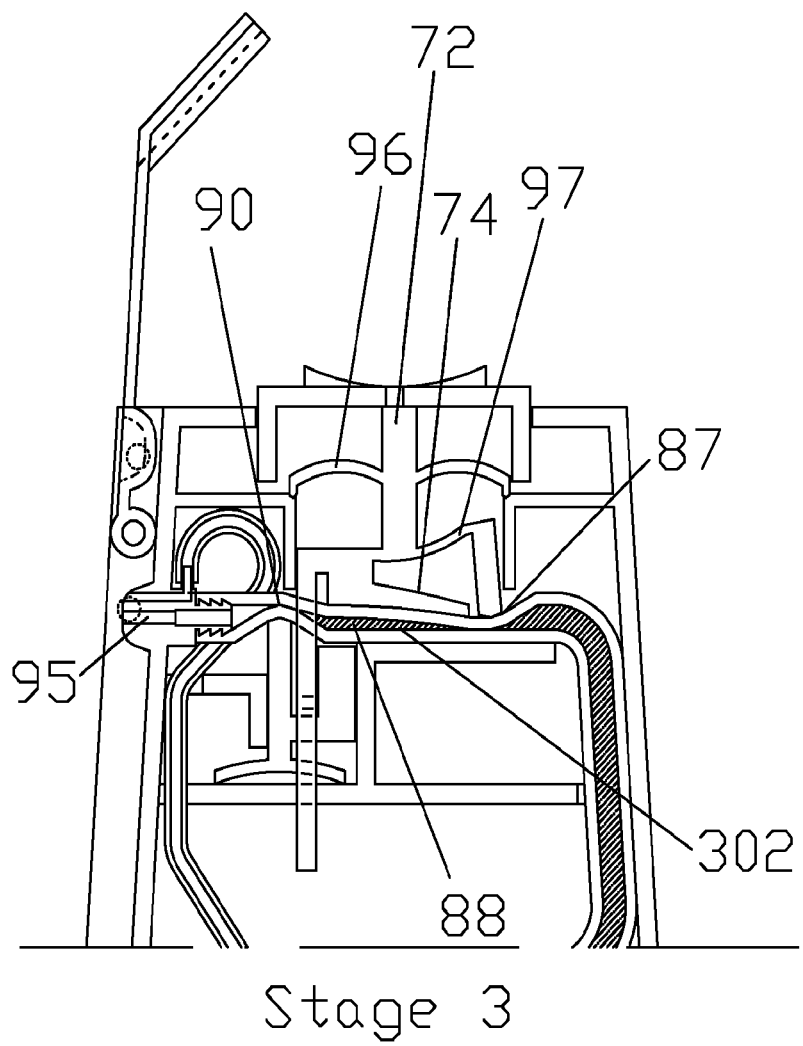
FIG. 6a shows a section view of the second preferred embodiment of the invention, with the third stage of pump operation being shown.
Figure 6B:
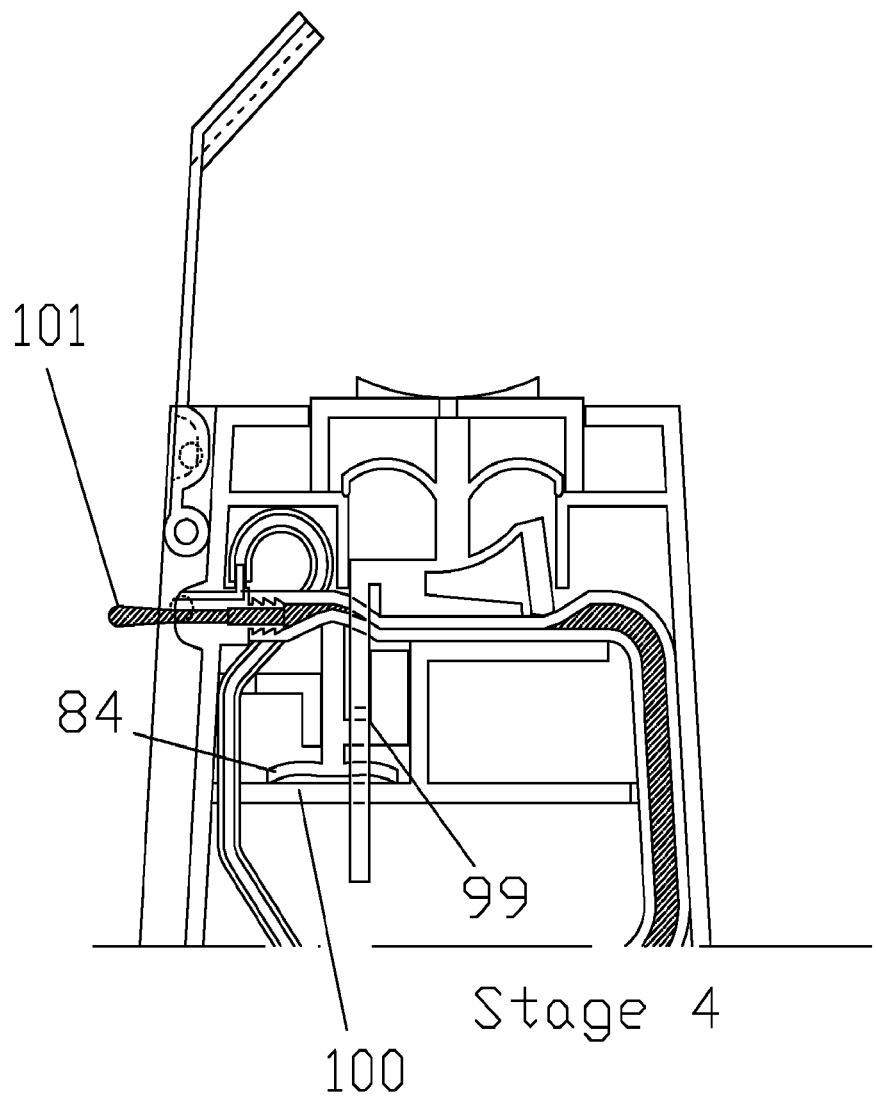
FIG. 6b shows a section view of the second preferred embodiment of the invention, with the fourth stage of pump operation being shown.

FIG. 6a shows a section view of the second preferred embodiment of the invention, with the third stage of dispenser operation being shown. FIG. 6b shows stage 4 is the discharging stage. For clarity purposes, some elements are not marked in FIGS. 6a and 6b. The denominations of such elements may be found in FIGS. 5a and 5b and other related Figures. As shown in FIG. 6a, when the push button 21 is pressed further downward, the sloped shoe 74 starts to press against the outside of the tube 11, deforming squeezing section 302 and the dosing chamber 88 in between the top anvil 75 and the bottom anvil 83, pressurizing the fluid enclosed in the dosing chamber 88. The pressing surface of the sloped shoe 74 is sloped so that the part of the squeezing section 302 closer to the second pressing point 87 gets into contact with the sloped shoe 74 before the first pressing point 90. Such a design allows the sloped shoe 74 to drive the fluid in the dosing chamber 88 towards the first pressing point 90, which is closer to the outlet orifice 95, facilitating the discharging process.

At the same time, the pressing plate connector 97 starts to bend, allowing further movement of the sloped shoe 74. As shown in FIG. 6, stages 3 and 4, the sloped shoe 74 is permitted to deform the tube 11 only when the top anvil 75 and the bottom anvil 83 are both closing off the bore 66 of the tube 11, at respective points 90 and 87.

As shown in FIGS. 5a and 5b and FIG. 6b, pressing the push button 21 further downward results in the contact between the pressing plate block 77 and side branch 85 at a contact point 99. Since the pressing plate block 77 is fixed on the pressing plate leg 76, the downward motion of the pressing plate 72 moves the pressing plate block 77 down, which further presses the side branch 85 and pushes down the anvil plate 82 as a whole. Consequently, the bottom anvil 83 is pressed down by pressing plate block 77 on the pressing plate 72 to release the restriction of the tube 11 at the first pressing point 90, and the fluid contained in the dosing chamber 88 is then free to escape under pressure through outlet orifice 18, as shown as a jet stream 101 in FIG. 6b. The engagement of pressing plate block 77 on the pressing plate leg 76 of the pressing plate 72 with the side branch 85 on the anvil plate 82 forces the first double leaf springs 84 against a stop plate 100—thus bending the first double leaf spring 84. As shown in FIG. 6b, in the discharge stage, the pressing plate connector 97, the first double leaf spring 84, the second double leaf spring 73, and the sloped shoe 74 are all bent and/or compressed. Such bending stresses may all serve to return the various components of the fluid dispenser 1 to their rest positions, once the operating force is removed from push button 21, while afterwards the bent or compressed components are restore to their un-stressed states.

Figure 7:
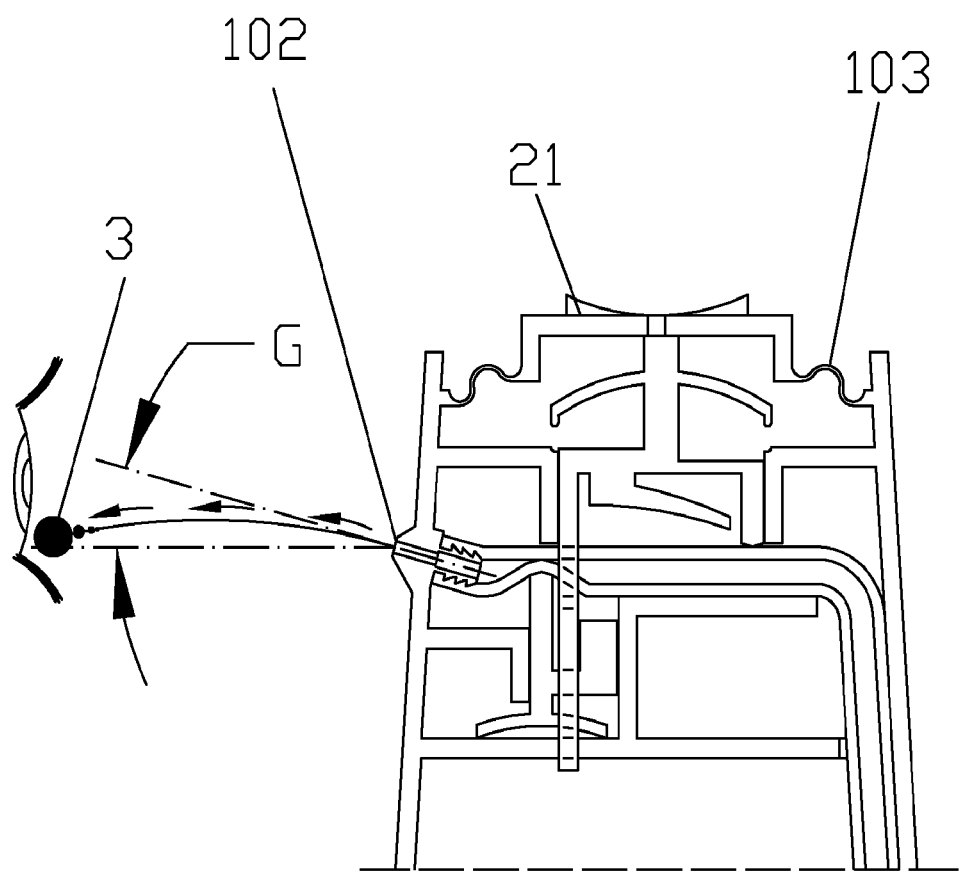
FIG. 7 shows a section view of the second preferred embodiment of the invention, with the outlet orifice inclined upward.

FIG. 7 shows a section view of the second preferred embodiment of the invention, with the outlet orifice 102 inclined upward, and with an alternate attachment for the operating button 21. Referring to FIG. 1b, after discharge from the outlet orifice 18, the droplets 3 take a projecting path and feed into the eye 5 of a patient. When the outlet orifice 18 is leveled, the trajectory of the droplets 3 tends to head lower than the outlet orifice 18 due to gravity. As shown in FIG. 7, outlet orifice 102 may be inclined upward at angle G from the level plain to compensate for gravitational effects on the droplets 3 emitted from the fluid dispenser.

Also shown in FIG. 7 is a flexible diaphragm 103 attaching the push button 21 to the dispenser case 10. In the embodiments shown in FIGS. 1-6, the push button 21 is not directly and physically connected to the dispenser case 10. Using the flexible diaphragm 103 enables the push button 21 to be linked to the dispenser case 10, eliminating the constriction resulted from the contact of the push button 21 with the dispenser case 10. Moreover, using the flexible diaphragm 103 may form a seal, preventing the contamination of the interior of the fluid dispenser 1.

The fluid dispenser 1 may include attachments and accessories to facilitate the dispensing process, improve control and convenience, and suit the needs of different purpose. FIGS. 8-21 illustrate the different designs that may improve the use of the fluid dispenser 1. Some structures are shown with the design of the first preferred embodiments, while some others are shown with the second preferred embodiment. It should be noted that the features shown in FIGS. 8-21 may be used for either embodiment.

As indicated in the descriptions for FIGS. 2a, 2b, and 2c, the dropper bottle 34 and the holding tank 20 in combination may serve as a reservoir for the fluid to be dispensed. In addition, the specific design of the reservoir may vary. FIG. 8 shows a section view of a part of the fluid dispenser 1 having a conventional dropper bottle 34 attached to the dispenser, the conventional dropper bottle 34 together with a holding tank 20 acting as a reservoir for the fluid to be dispensed.

As shown in FIG. 8, there is a holding slot 68 that allows for the installation of a conventional dropper bottle 34. The dropper bottle 34 contains the fluid, and is either screwed or snapped into the holding slot 68 in such a way as to prevent the later removal of the dropper bottle 34. Removal of the dropper bottle 34 is disadvantageous because the sterility for the dispenser cannot be maintained over an extended period—as might occur if the dispenser were used with more than one dropper bottle. Removal of the dropper bottle 34 is prevented by one or more catches 38 which snap over dropper bottle flange 61. The dropper bottle 34 in this design is connected to the dispenser with the nozzle having first been removed from the dropper bottle 34. This differs from the installation shown in FIG. 1 in which the nozzle is not removed from the dropper bottle 34 prior to installation into the dispenser. In FIG. 8, the dropper bottle 34 is sealed except for a drain hole 117.

As shown in FIG. 8, this design provides a holding tank 20 which accommodates a certain volume of fluid, wherein the volume may vary depending on the size of the fluid dispenser 1. Generally, the volume may be up to the full contents of a traditional dropper bottle—around 30 ml. Preferably, dropper bottles ranging in volume from 3 ml to 15 ml would be used. The holding tank 20 may include a transparent or translucent sight glass 110, so that the amount of fluid held in the tank can be clearly seen from the outside. Although it is possible to decant the entire content of the dropper bottle 34 into the holding tank 20, the dispenser can be operated with only a partial filling of the holding tank 20. Complete decanting of the contents of the dropper bottle 34 can, therefore, be accomplished in stages via drain hole 117.

FIG. 9 shows the section view of a fluid dispenser 1 with a conventional dropper bottle 34, complete with its nozzle (not shown) and outer cap 39, acting as the external reservoir for the fluid to be dispensed. Here no holding tank is present and the dropper bottle 34 is used directly as the source of the fluid to be dispensed. This design is an alternative method for installing the dropper bottle 34 into a fluid dispenser 1. This embodiment has a dropper bottle 34 located within a compartment 124 so that the bottom of the dropper bottle 34 is punctured by a hollow spike 123 projecting from a bulkhead 121. The bulkhead 121 accommodates the tube 11, which delivers the fluid to the pump mechanisms including the hinge-pieces, the push button, the push plate, and the cantilever plate. Venting to reservoir is accomplished in this design by unscrewing and loosening the outer cap 39 of the dropper bottle 34. After use, the outer cap 39 may be tightened to protect the liquid contents from airborne contamination.

Figure 10:
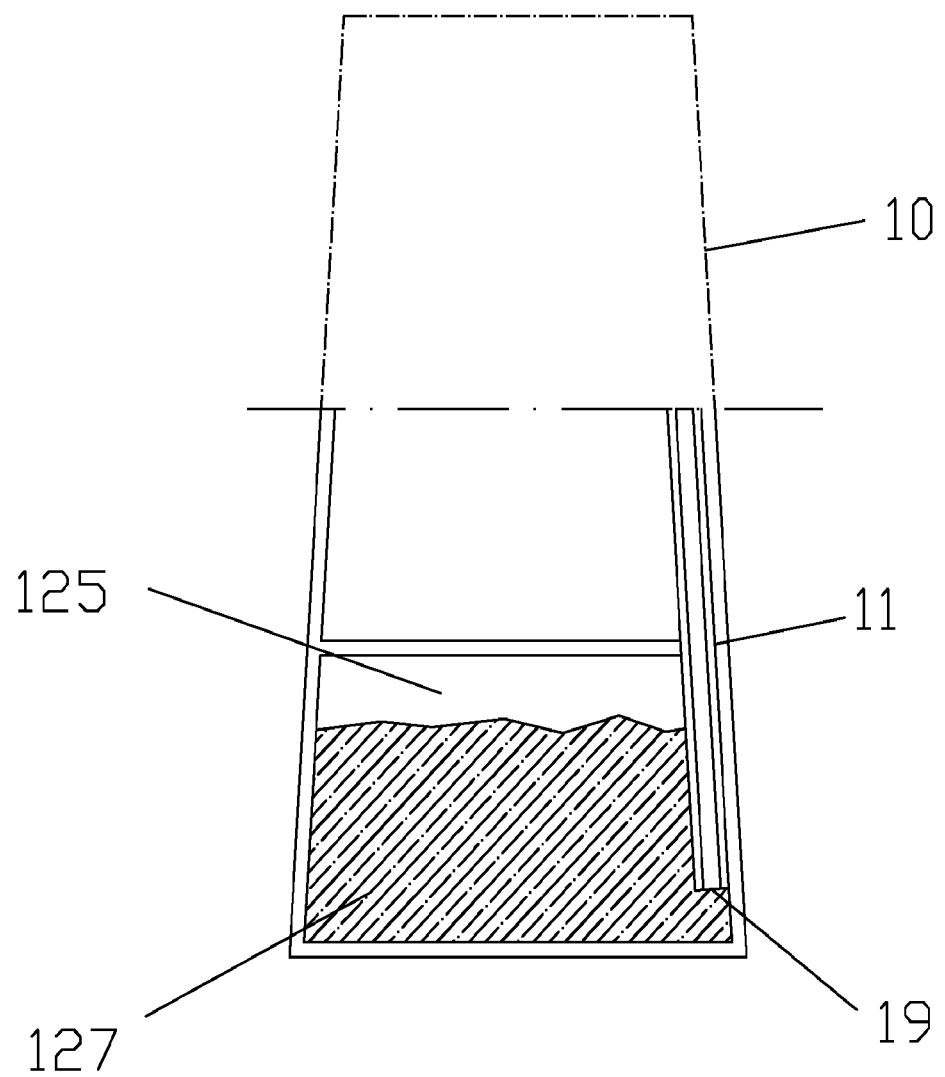
FIG. 10 shows a section view of a first design of an integral reservoir for the fluid dispenser.

FIG. 10 shows a section view of a first design of an integral reservoir for the fluid dispenser. An integral reservoir is a non-removable part of the dispenser case 10 and there is preferably no refilling mechanism such as a dropper bottle directly attached to it. FIGS. 10-14 illustrate several designs that incorporate an integral reservoir. FIG. 10 shows a reservoir 125, which feeds the pump head with liquid 127 via the inlet end 19 of the tube 11. Here, this reservoir 125 design is preferably used for the pump mechanisms shown in FIGS. 1-4. However, this design may also be used for the embodiments shown in FIGS. 5-6, if the vent tube 93 is added and extends into the reservoir 125.

FIG. 11 shows a section view of a second design of an integral reservoir for the fluid dispenser 1 which incorporates a collapsible bag 131 holding the fluid to be dispensed. The collapsible bag 131 is housed within a compartment 130 and it is connected to tube 11. The collapsible bag 131 is preferably made of flexible materials that are impermeable to air or liquid. This reservoir design would allow fluids that are free of preservatives to be used for the dispenser, since the concern for atmospheric contaminants is eliminated due to the impermeability of the collapsible bag 131. FIG. 11 also shows the vent tube 93 (as shown in FIGS. 5 and 6) having a reservoir end 133. As the collapsible bag 131 feeds fluid to the pump mechanisms, air may enter the compartment 130 through the vent tube 93 and out of the reservoir end 133, preventing the reduction of air pressure around the collapsible bag 131.

Figure 12:
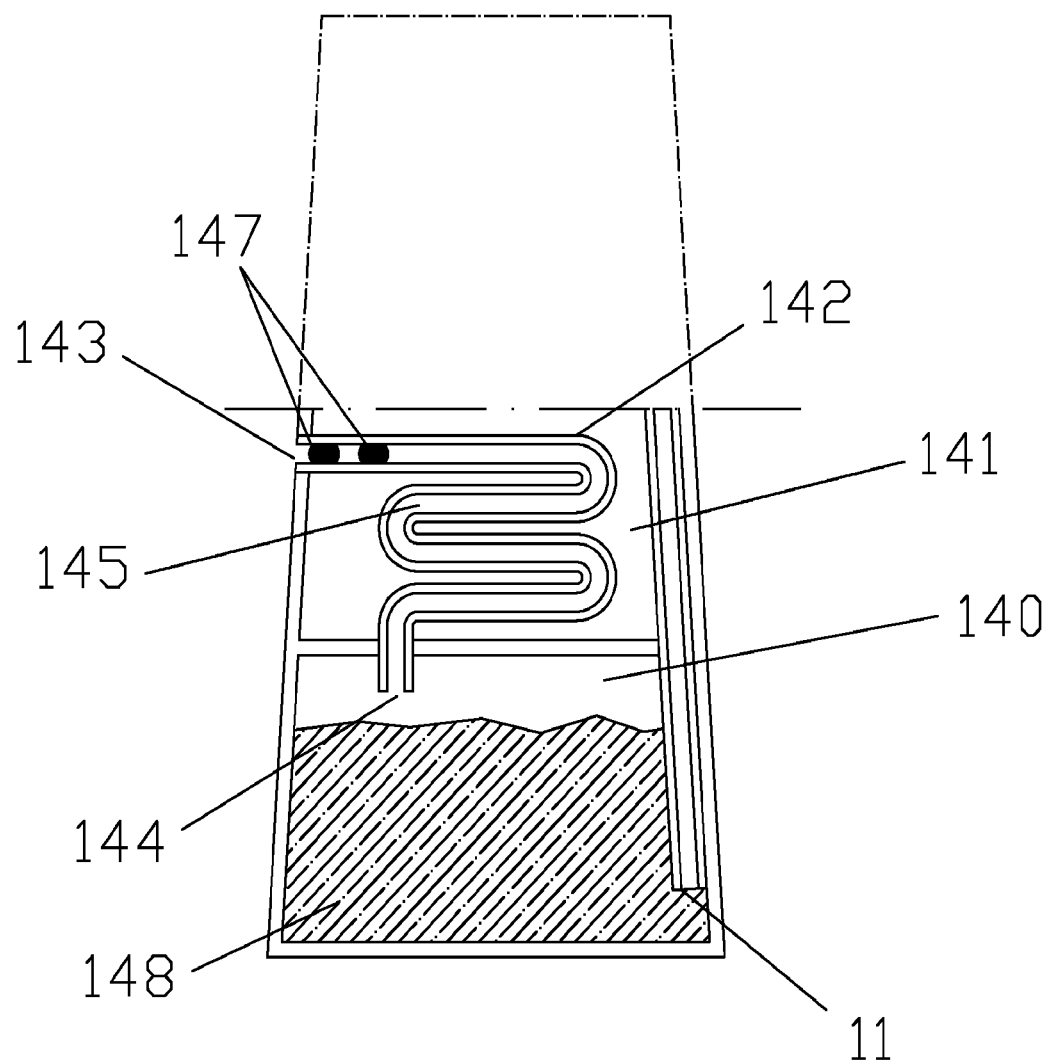
FIG. 12 shows a section view of a third design of an integral reservoir for the fluid dispenser, the third design allows restoration of atmospheric pressure within the integral reservoir as the fluid is being dispensed.

FIG. 12 shows a section view of a third design of an integral reservoir for the fluid dispenser 1, the third design allowing restoration of atmospheric pressure within the integral reservoir as the fluid is being dispensed. Shown in FIG. 12 is an elongated vent path utilizing an accessory tube 142 having a tube bore 145 housed within an upper compartment 141. The accessory tube 142 incorporates one or more small beads of liquid 147 at the input end 143 of tube bore 145. The tube bore 145 of accessory tube 142 terminates at reservoir end 144 in the headspace 140 above the fluid 148 being dispensed and forms a continuous path along which beads of liquid 147 may travel. As fluid 148 is dispensed from the dispenser through tube 11, a partial vacuum is created in headspace 140 and tube bore 145 which pulls beads of liquid 147 along tube bore 145 towards the reservoir end 144. These beads of liquid 147 discourage the passage of contaminants from the atmosphere into the fluid 148 by acting as a barrier, and would enable fluid 148 to be dispensed that are free of preservatives. Headspace 140 and tube bore 145 may contain air, nitrogen, or any other inert gas. The accessory tube 142 is preferred to be coiled in the upper compartment 141 to increase the length of the accessory tube 142 so that a significant volume of fluid 148 to be dispensed before the small beads of liquid 147 enters the headspace 140.

Figure 13:
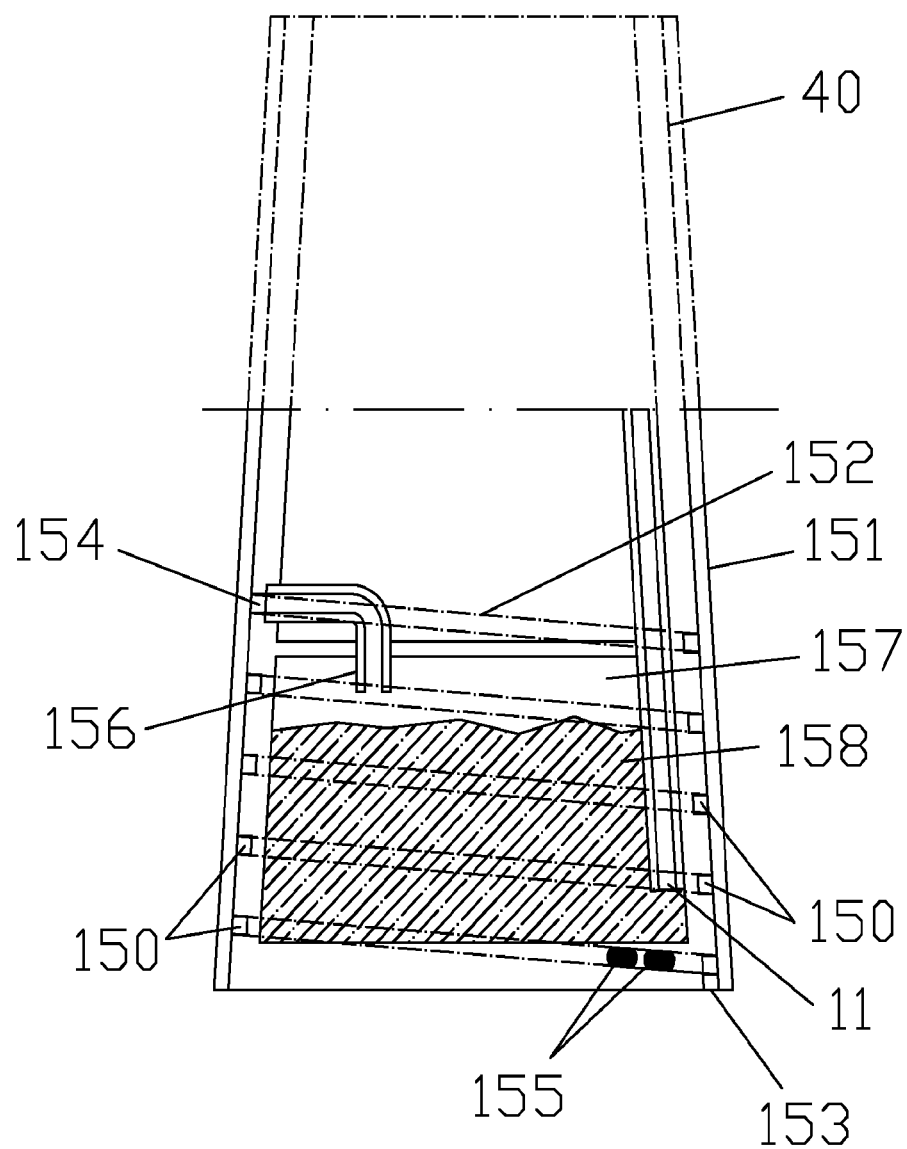
FIG. 13 shows a section view of a fourth design of an integral reservoir for the fluid dispenser, the fourth design allows restoration of atmospheric pressure within the integral reservoir as the fluid is being dispensed.

FIG. 13 shows a section view of a fourth design of an integral reservoir for the fluid dispenser, the fourth design allows restoration of atmospheric pressure within the integral reservoir as the fluid is being dispensed. With reference to FIG. 13, a helical vent arrangement is shown, comprising a helical slot 152 running around the periphery of a dispenser case 10 and an outer cover 151 such that when assembled the two parts define an enclosed helical vent path 150. The helical vent path 150 has an outer end 153 and an inner end 154, with said inner end 154 being connected to the headspace 157 above the liquid 158 by means of an elbow 156. Said headspace 157, elbow 156, and the helical vent path 150 contain either air, nitrogen, or some other inert gas. In close proximity to the outer end 153 of the helical vent path 150, one or more small beads of liquid 155 are added, which isolate the gas within the helical vent from any contact with atmospheric air that is external to the dispenser. As-liquid 158 is drawn from its reservoir via tube 11 to the pump mounted above (not shown in FIG. 13), the bead or beads of liquid 155 are drawn along the helical vent path 150 along with the entrapped air, nitrogen, or other inert gas, to prevent the formation of a vacuum within headspace 157, elbow 156, and vent path 150. A tube may be built into the helical vent path 150 to ensure impermeability.

Figure 14:
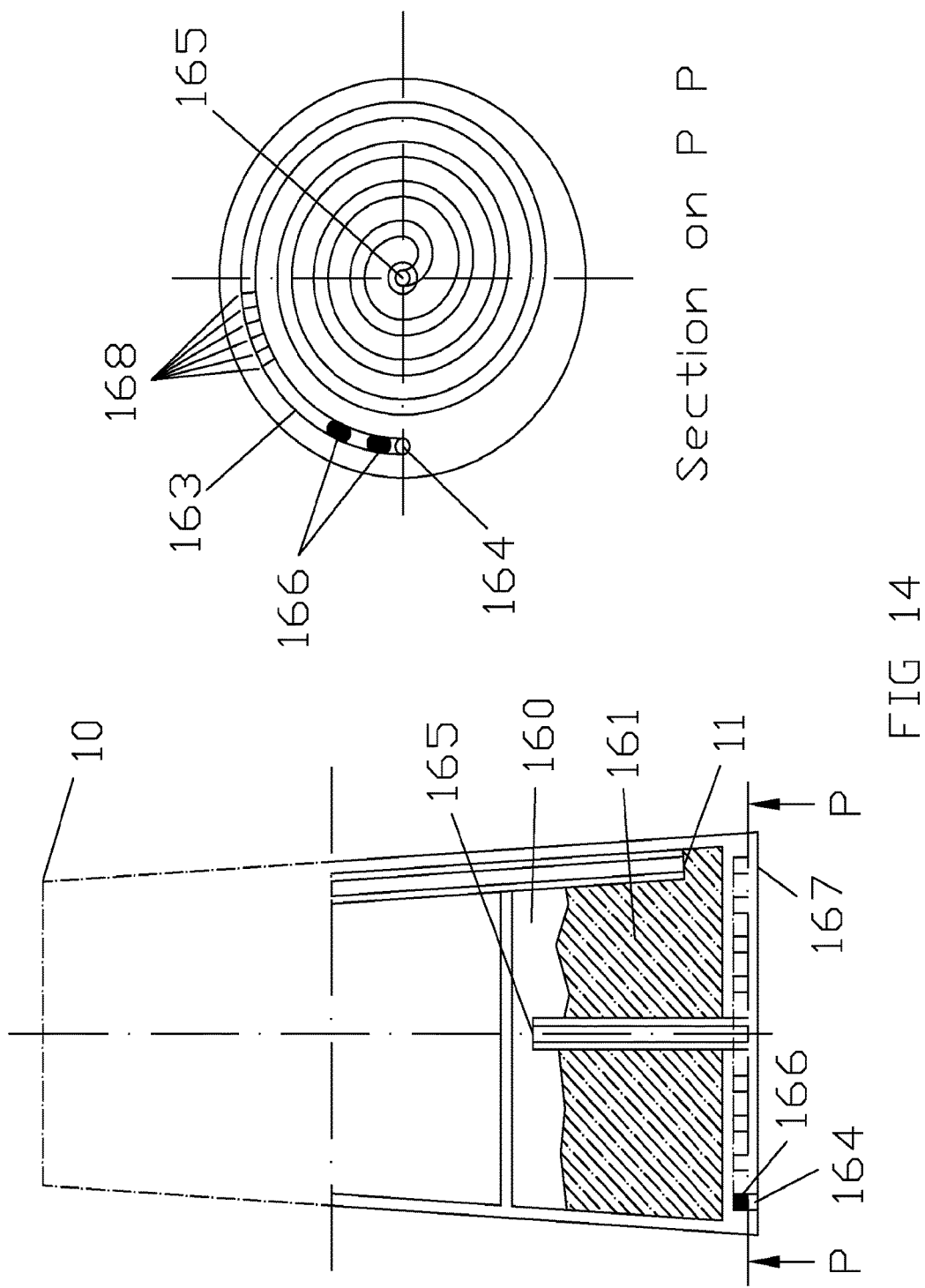
FIG. 14 shows a section view of a fifth design of an integral reservoir for the fluid dispenser as well as an inverted plan view of a spiral groove that helps to restore atmospheric pressure within the integral reservoir as the fluid is being dispensed.

The left panel of FIG. 14 shows a section view of a fifth design of an integral reservoir for the fluid dispenser. The right panel of FIG. 14 shows an inverted plan view of a spiral groove 163. Points P and P' serve as indicators for the section view. The design shown in FIG. 14 is similar to that shown in FIG. 13. In FIG. 14, the vent path is arranged as a spiral groove 163 disposed into a base of the dispenser case 10, with said base then covered by a sealing plate 167. One end of the spiral groove 163 coincides with a hole 164 projecting through the sealing plate 167. The inside of the spiral groove 163 terminates at an upstanding pipe 165 which is attached to sealing plate 167 such that the bore of the upstanding pipe 165 and the spiral groove 163 form a continuous vent pathway, which terminates at the top of the pipe 165 within the headspace 160 above the liquid 161 in an integral reservoir. The spiral groove 163 and upstanding pipe 165 and headspace 160 above the liquid being dispensed 161 are filled with air, nitrogen, or some other inert gas. Such gas serves to restore atmospheric pressure in the headspace 160 when the liquid 161 is being dispensed. There is a small bead or beads of liquid 166 in the spiral groove 163 close to the hole 164. The bead or beads of liquid 166 entrap the inert gas in the spiral groove 163 and separate the inert gas from external air. The beads of liquid 166 are drawn along the spiral groove 163 in concert with the fluid 161 being dispensed by the dispenser through tube 11.

In FIGS. 13 and 14, the inner face of the helical vent path 150 and the spiral groove 163 may be engraved or have other markings 168 indicating the contents of the integral reservoir, such that the bead or beads of liquid may serve as a pointer against the markings indicating that liquid is being depleted from the reservoir. Such marking may be used to indicate the remaining volume of the fluid held within the dispenser.

Figure 15A:
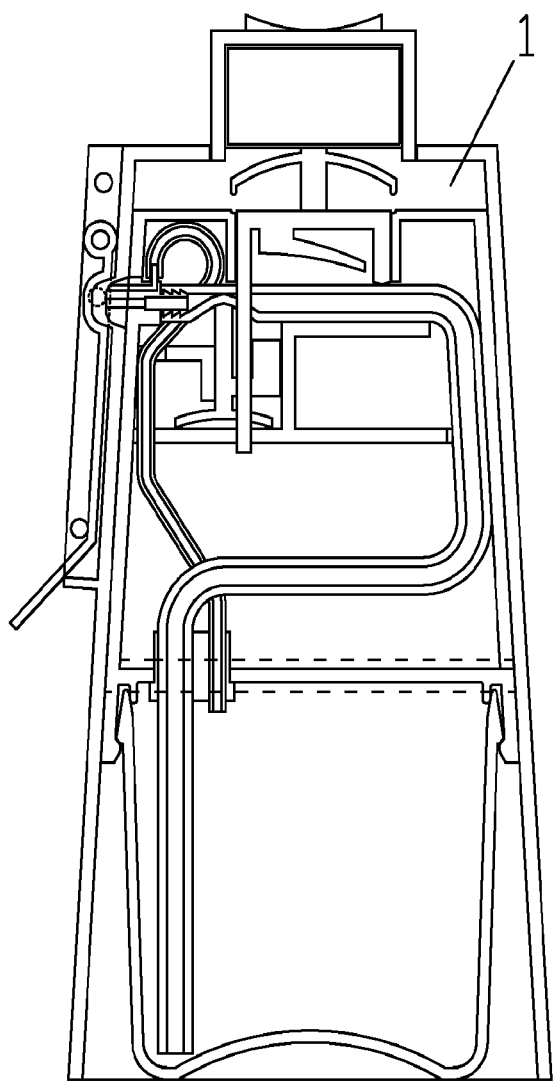
FIG. 15a shows a dispenser with a removable reservoir.
Figure 15B:
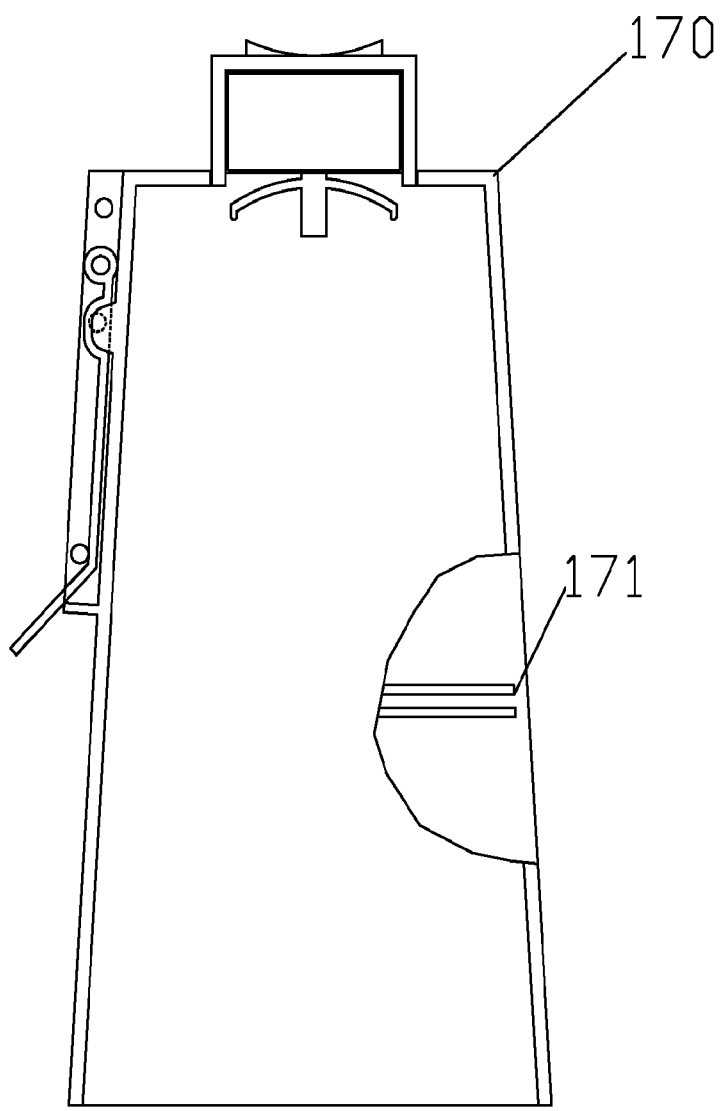
FIG. 15b shows a dispenser case which accommodates a removable reservoir.
Figure 15C:
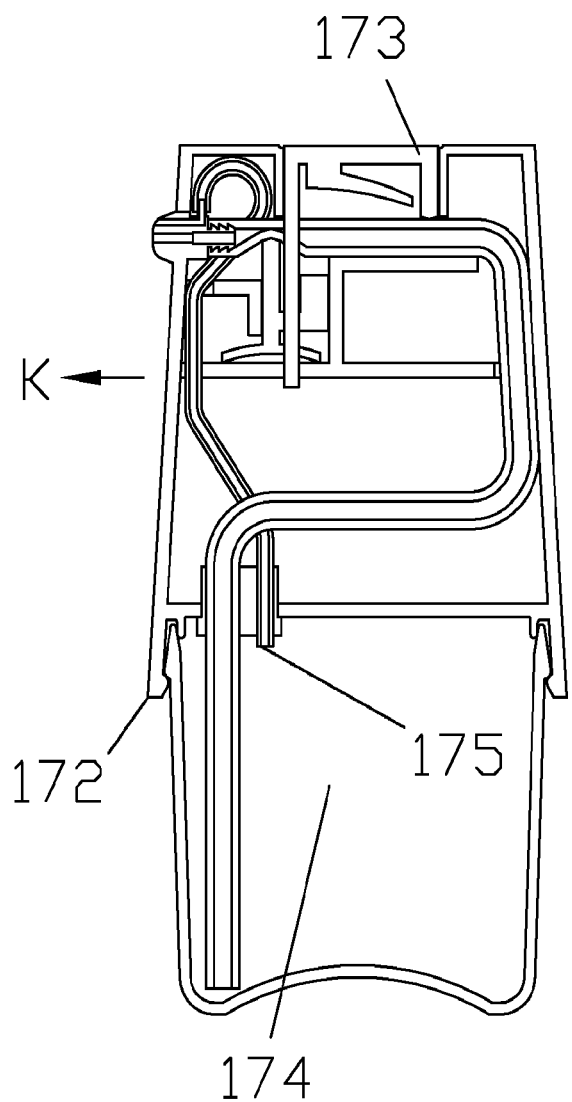
FIG. 15c shows a removable reservoir.

FIGS. 15*a*, 15*b*, and 15*c* show a removable reservoir, incorporating some parts of the pump mechanism. The design shown in FIGS. 15*a*, 15*b*, and 15*c* uses the second preferred embodiment of pump mechanism as illustration. Here, the fluid dispenser 1 may be separated into a dispenser outer case 170 and a functional unit 173. FIG. 15*a* illustrates the fluid dispenser 1 in an assembled form. FIG. 15*b* is the dispenser outer case 170, with a partially front and partially sectional view. FIG. 15*c* shows the functional unit 173. Arrow K serves to indicate how the functional unit 173 may be inserted into the dispenser outer case 170. Shown in FIG. 15*b* is a connecting interface 171. Shown in FIG. 15*c* is a functional unit 173 having a magazine 172. The functional unit 173 may slide into the dispenser outer case 170 wherein the magazine 172 is slidably connected within the connecting interface 171.

Figure 16A:
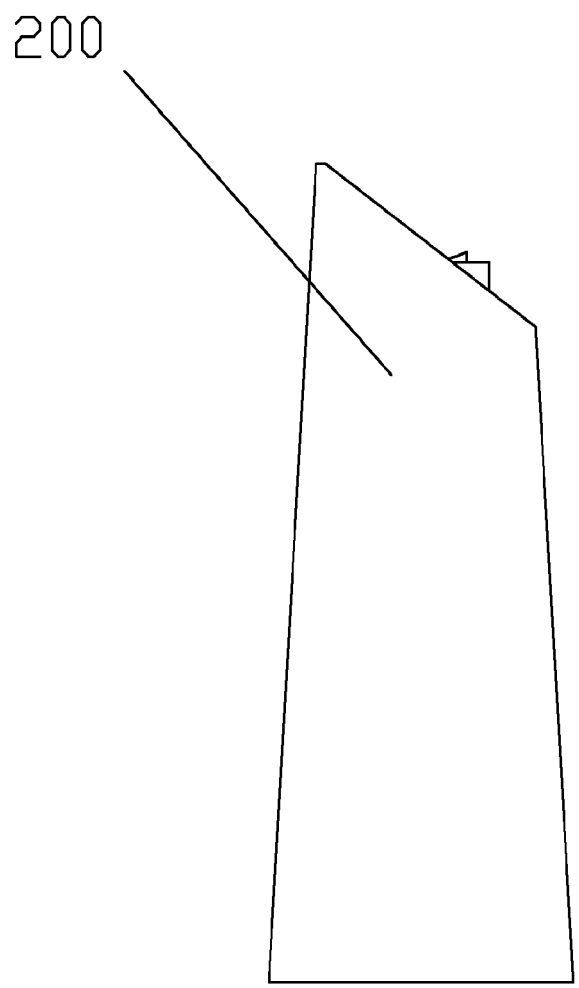
FIG. 16a shows the outer contours of one embodiment of the fluid dispenser.
Figure 16B:
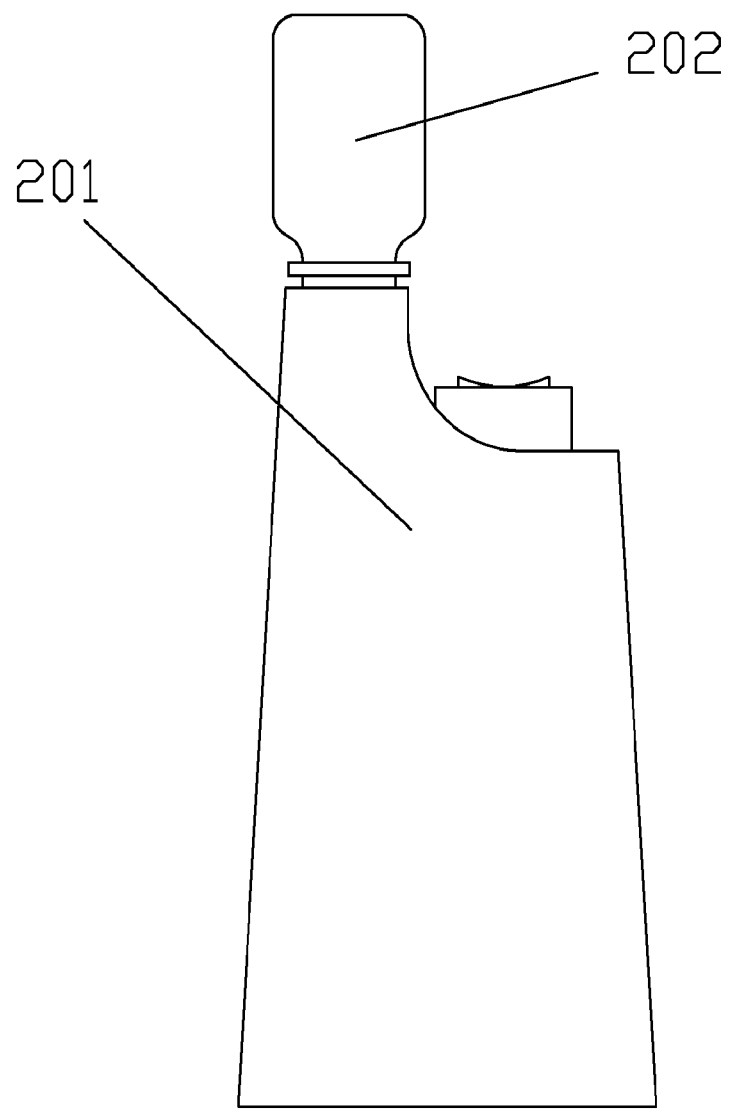
FIG. 16b shows the outer contours of another embodiment of the fluid dispenser, with the embodiment having a conventional dropper bottle acting as the reservoir for the fluid to be dispensed.

FIGS. 16*a* and 16*b* show the outer contours of two embodiments of the fluid dispenser. Shown in FIG. 16*a* is a basic outer form of a dispenser case 200, where the fluid to be dispensed is housed in an integral reservoir. Alternatively, as shown in FIG. 16*b*, a conventional dropper bottle 202 could be inverted and then disposed onto the top of the dispenser case 201, serving to provide the fluid to be dispensed.

Figure 17A:
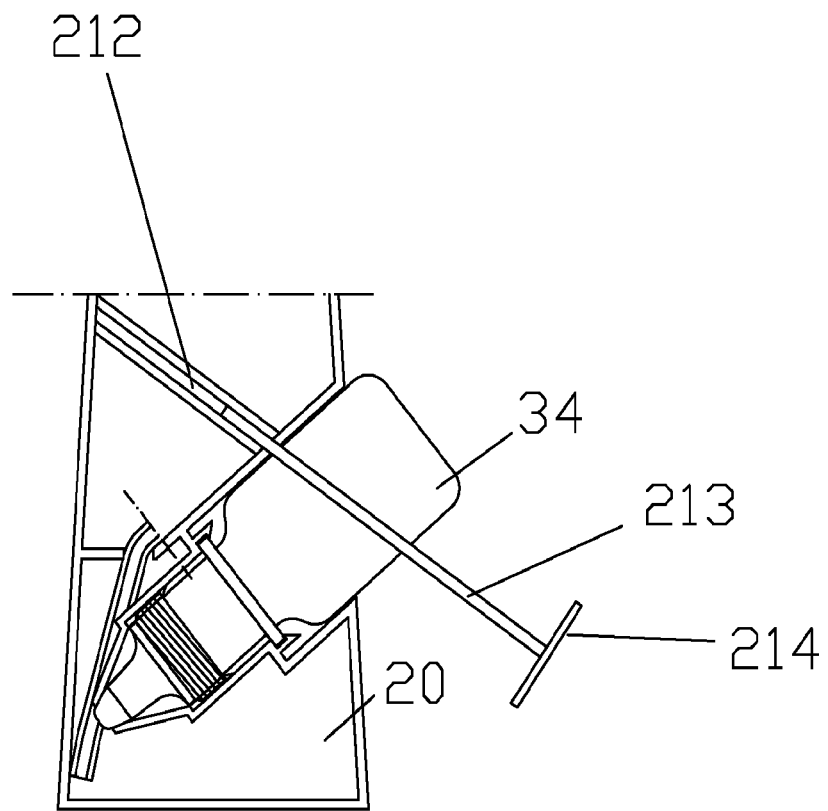
FIG. 17a shows a section view of a first refilling accessory for squeezing a dropper bottle, which is loaded into a fluid dispenser, in order to decant fluid into the dispenser.
Figure 17B:
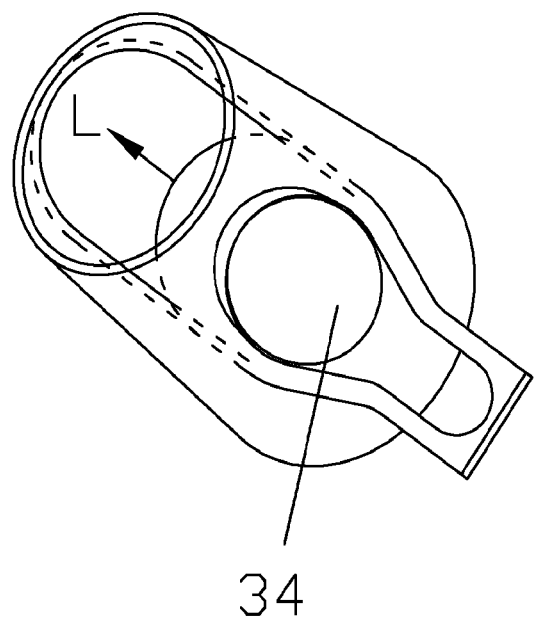
FIG. 17b shows a partial plan view of a first refilling accessory for squeezing a dropper bottle, which is loaded into a fluid dispenser, in order to decant fluid into the dispenser.
Figure 17C:
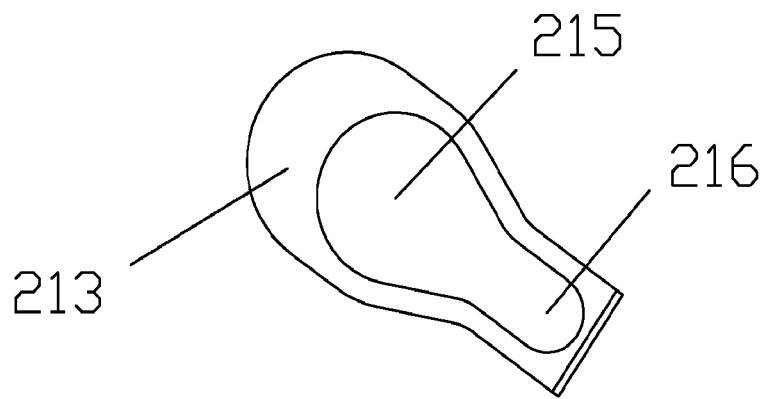
FIG. 17c shows a top view of a slide plate.

FIGS. 17*a*, 17*b*, and 17*c* shows a first refilling accessory for squeezing a dropper bottle 34, which is loaded into a fluid dispenser, in order to decant fluid into the holding tank 20 FIG. 17*a* is a side view of a sliding plate 213 and FIG. 17*c* is a top view of the slide plate 213, which has an enlarged opening 215 connected to a smaller opening 216. The enlarged opening 215 is slightly larger than the diameter of the dropper bottle 34 and the smaller opening 216 is smaller than the bottle diameter. There is a track 212 into which the sliding plate 213 may be inserted. FIG. 17*b* is a top perspective view of the dispenser when the sliding plate 213 encircles the dropper bottle 34. The enlarged opening 215 is initially aligned to the dispenser in such a way as to permit the bottle 34 to be inserted into the enlarged opening 215 and the sliding plate 213 is inserted the dispenser by sliding into the track 212. Once so inserted, the sliding plate 213 is then pushed, by means of plate 214 which attaches to the sliding plate 213, inward along track 212 in the direction of Arrow L, thus forcing the dropper bottle 34 to conform to the smaller opening 216. This manipulation of the dropper bottle 34 causes it to dispense fluid into the holding tank 20.

Figure 18A:
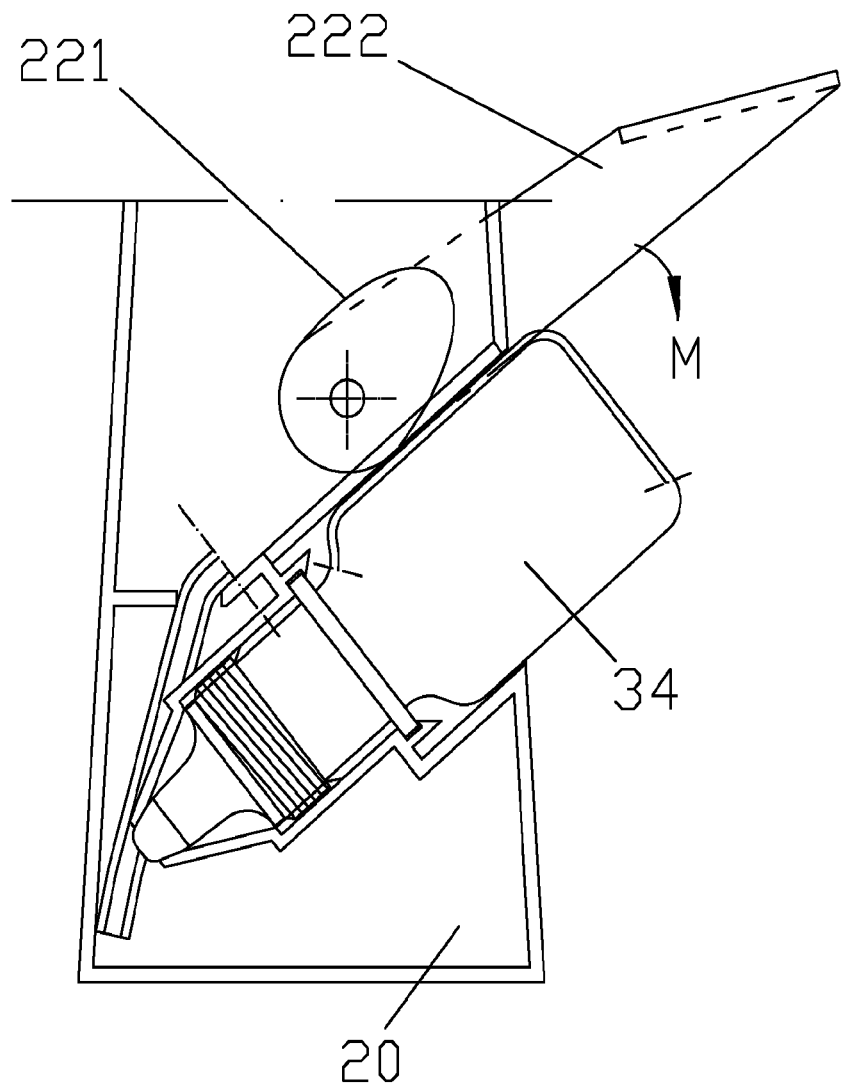
FIG. 18a shows a second refilling accessory for squeezing a dropper bottle, which is loaded into a fluid dispenser, in order to decant fluid into the dispenser. The refilling accessory is shown in its un-operated position.
Figure 18B:
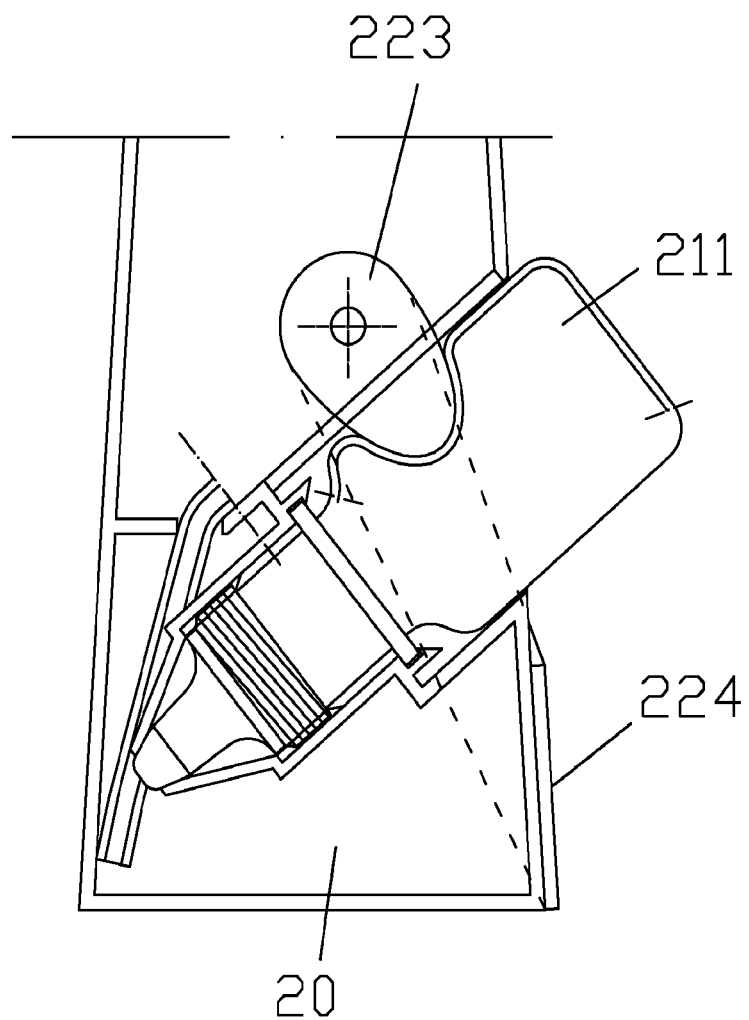
FIG. 18b shows a second refilling accessory for squeezing a dropper bottle, which is loaded into a fluid dispenser, in order to decant fluid into the dispenser. The refilling accessory is shown in its operated position.

FIGS. 18a and 18b show a second refilling accessory for squeezing a dropper bottle 34 which is loaded into a fluid dispenser, in order to decant fluid into the dispenser. In this design a cam 221 at a position as shown in FIG. 18a is coupled to a lever 222 are held in an elevated position to permit the dropper bottle 34 to be inserted into the dispenser. At the first position, the dropper bottle 34 is not squeezed. Upon rotation of the lever 222, in the direction of Arrow M into a position shown in FIG. 18b, the cam 221 rotates into a position shown in the FIG. 18b and squeezes the outside of the dropper bottle 34—thus decanting liquid into the holding tank 20.

Figure 19A:
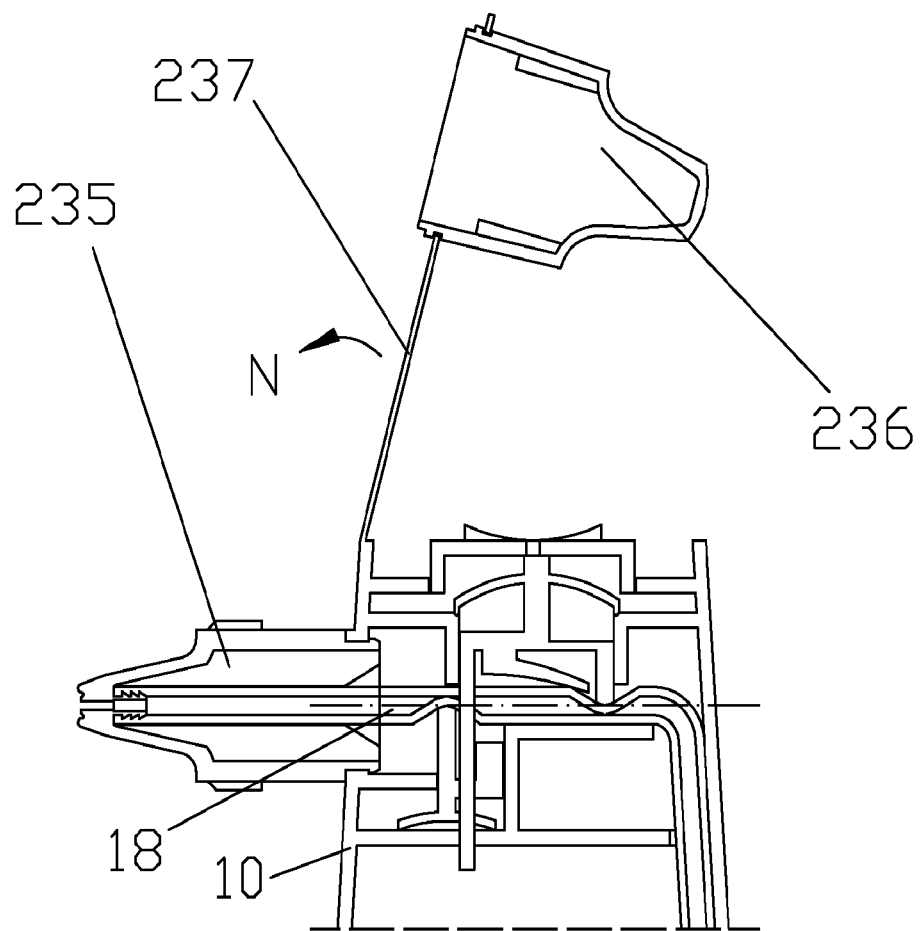
FIG. 19a shows a section view of an overcap closure attached to the dispenser, with the overcap unattached.
Figure 19B:
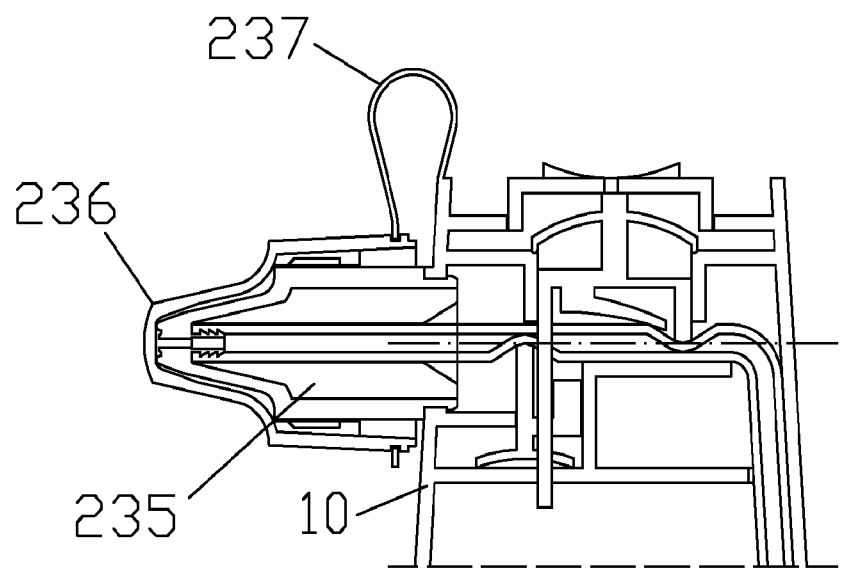
FIG. 19b shows a section view of an overcap closure attached to the dispenser, with the overcap attached.

FIGS. 19a and 19b show a section view of an overcap closure mechanism attached to the dispenser. Shown in FIG. 19 is a cap 236 which screws or snaps onto an extended outlet 235. The extended outlet 235 may be snapped (shown in FIG. 19) or screwed to the dispenser case 10 to extend the outlet orifice 18. Such a nozzle extension may be used to deliver ear drops. As shown in FIG. 19a, cap 236 may be retained to the dispenser by means of a flexible tie 237, which bends in the direction of Arrow N to allow the cap 236 to be secured to the extended outlet 235. The cap 236 may be snapped or screwed to the extended outlet 235. The cap 236, or any alternative designs, may prevent the interior of the fluid dispenser to be contaminated by the ingress of dirt. Different outlet designs may be used for different purposes. One may be shaped for ophthalmic applications; another (as shown in FIGS. 19a and 19b) may be of elongated tubular form for use in otic (ear drop), or nasal, or other, applications.

Figure 20A:
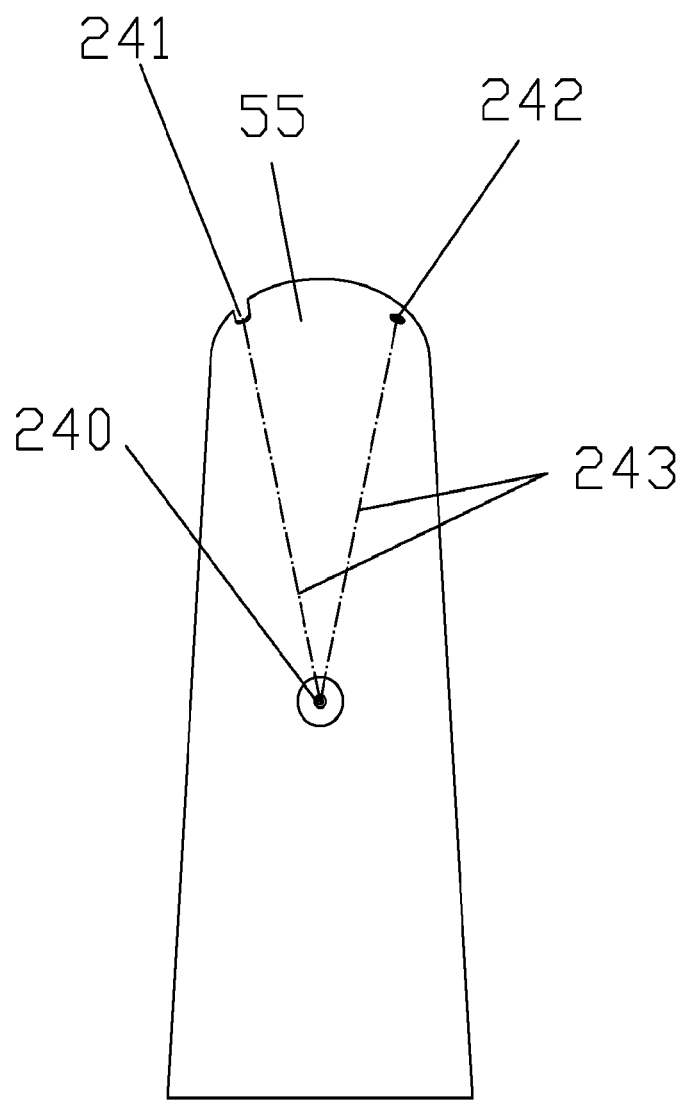
FIG. 20a shows a first targeting accessory for aiming the fluid to be dispensed to a target, as seen from the front.
Figure 20B:
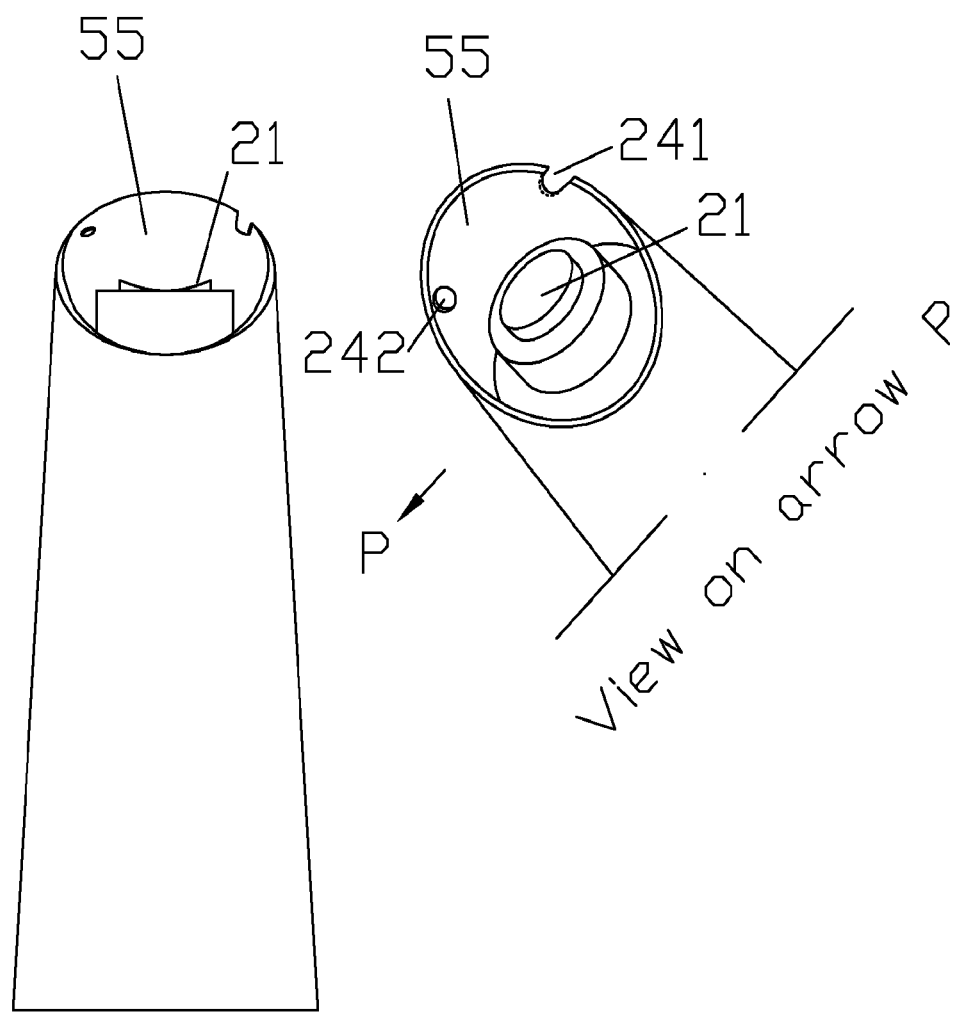
FIG. 20b shows a first targeting accessory for aiming the fluid to be dispensed to a target, as seen from the rear.

FIGS. 20a, 20b show a first targeting accessory for aiming the fluid to be dispensed to a target, such as an eye. FIG. 20a is a front view showing an outlet orifice 240; FIG. 20b is partly back view and partly back top perspective view showing the push button 21. For clarity purposes, as shown in FIG. 20a, a hole 242 is on one side and a slot 241 is on the other side of the extended shroud 55. However, it should be noted that preferably, on the extended shroud 55 there should be a pair of holes 242 or a pair of slots 241. The holes 242 or the slots 241 are angled in such a way that the two holes or the two slots are directed to point by triangulation to a position in space in front of the outlet orifice 240 consistent with the trajectory of the dose which the dispenser discharges. Alternatively, a pair of piezo-electric lights (such as LED's—not shown in FIG. 20a or FIG. 20b) may be provided in place of holes 242 or slots 241. The lights may be triggered by pressing the push button 21, and may offer the same triangulation of the position of the dose at a given distance in front of the outlet orifice 240.

Figure 21:
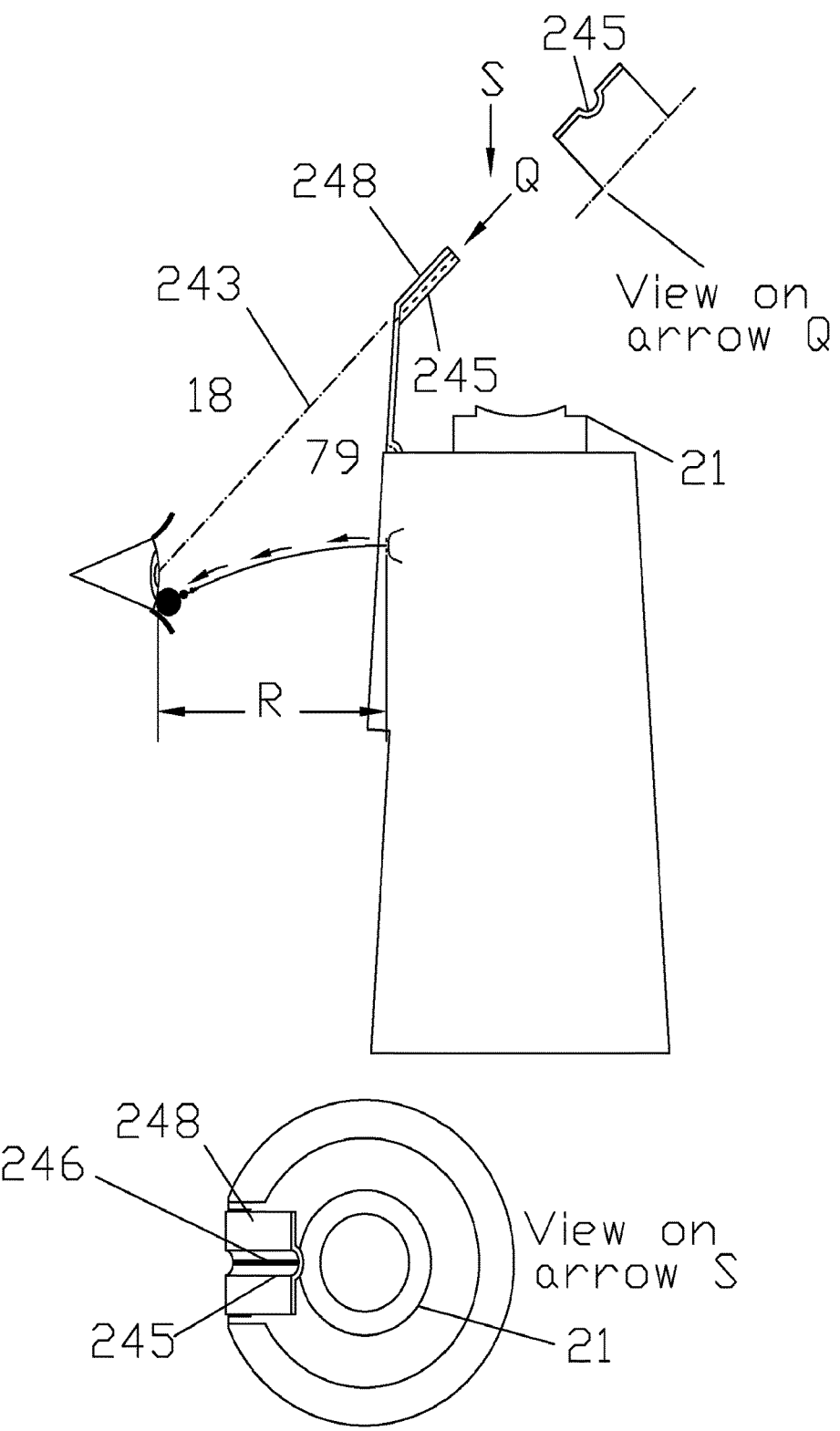
FIG. 21 shows a second targeting accessory for aiming the fluid to be dispensed to a target.

FIG. 21 shows a second targeting accessory for aiming the fluid to be dispensed to a target, such as an eye. The middle panel is a side view of a dispenser having a flip closure 79, as shown in FIGS. 5a and 5b. The flip closure 79 is positioned on top of the dispenser case and in the front side and has an upstanding guard 248 with a single groove 245 in the middle of the upstanding guard 248. A black line 246 may be added to the base of the groove 245 as a further aid to alignment, as shown in the bottom panel of FIG. 21. The bottom panel is a top view of the dispenser from the direction shown as Arrow S in the middle panel. The bottom panel illustrates the push button 21 and the upstanding guard 248. This single groove 245 may be directed to define one axis of triangulation, wherein a fixed distance R from the outlet orifice defines the second point of triangulation, such that axis 243 intersects with the eye a fixed distance R from the outlet orifice 18, as shown in the middle panel of FIG. 21. The top panel of FIG. 21 is a view from arrow Q in the top panel. A user of the dispenser may look from the view shown in the top panel and make aim to discharge fluids to the target.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed is:

1. A fluid dispenser for administering a fluid, comprising:
a dispenser case,
a reservoir, the reservoir holding a plurality of doses of the fluid,
a tube enclosed in the dispenser case, the tube having an inlet end and an outlet end, the inlet end being fluidly connected to the fluid in the reservoir, the outlet end being fluidly connected to an outlet orifice, wherein the tube is foldable along its length at a first fold point, closer to the inlet end, and a second fold point, closer to the outlet end, the angle of the folds at each of the first and second fold points being operable independently of one another to either at least partially open or close a bore of the tube and thereby enable or prevent fluid flow;
a squeezing section, being a segment of the tube defined between the first fold point and the second fold point in which at least a dose of the fluid may be retained; and
an actuating assembly, operable to be pressed against the squeezing section,
whereafter, independent of the pressure applied by the actuating assembly to the dose of the fluid within the squeezinq section, the angle of the second fold is subsequently caused to at least partially open the tube at the second fold point, with the first fold point remaining closed, releasing the dose to flow through the outlet end.

2. The fluid dispenser of claim 1, wherein the first fold point is a first articulating fold point, the second fold point is a second articulating fold point.

3. The fluid dispenser of claim 1, wherein the actuating assembly further comprises an anvil, the anvil being capable of being pressed against the squeezing section.

4. The fluid dispenser of claim 1, wherein the actuating assembly further comprises a push button having a first spring member attached to a lower part of the push button.

5. The fluid dispenser of claim 1, wherein the actuating assembly further comprises a first spring member attached to a lower part of a push button, a first hinge-piece and a second hinge-piece, the first hinge-piece being aligned against the squeezing section and the second hinge-piece being attached to the first spring member, wherein the anvil is attached to the second hinge-piece.

6. The fluid dispenser of claim 1, wherein the actuating assembly further comprises:
a cantilever plate attached to a push button, the cantilever plate having a cantilever plate opening with an enlarged portion,
a first spring member attached to a lower part of the push button, a first hinge-piece and a second hinge-piece, the first hinge-piece being aligned against the squeezing section and the second hinge-piece being attached to the first spring member, wherein the first hinge-piece is connected to a cantilever extension by a first pivot, the second hinge-piece is connected to the first hinge-piece with a second pivot, wherein pressing the push button causes the sliding of the first hinge-piece and the second hinge-piece in the cantilever plate opening before the second pivot goes through the enlarged portion of the cantilever plate opening, resulting in the repositioning of the second pivot, the second hinge-piece and the first hinge-piece, wherein the folding of the tube changes at the first articulating fold point, allowing the dose of the fluid to be discharged.

7. The fluid dispenser of claim 1, wherein the first fold point is a first pressing point, the second fold point is a second pressing point, and the tube is capable of being pressed at the first pressing point and a second pressing point, preventing the fluid to flow through the first pressing point and the second pressing point.

8. The fluid dispenser of claim 1, further comprising a vent tube having a first end and a second end, the first end connecting to a vent hole on the dispenser case and the second end connecting to the reservoir.

9. The fluid dispenser of claim 1, wherein the fluid is a formulation, solution, gel, or suspension.

10. The fluid dispenser of claim 1, wherein the reservoir comprises a dropper bottle attached to the dispenser case, the dropper bottle contains a plurality of the doses of the fluid, and the inlet end of the tube connects to the fluid contained in the dropper bottle.

11. The fluid dispenser of claim 1, wherein the reservoir comprises a holding tank, and a collapsible bag residing in the holding tank, the collapsible bag containing a plurality of the doses of the fluid.

12. The fluid dispenser of claim 1, wherein the reservoir comprises
 a holding tank integral to the dispenser case, the holding tank containing a plurality of doses of the fluid,
 an accessory tube having a tube bore, an input end and a reservoir end, the reservoir end fluidly connected to a headspace in the holding tank, the headspace being fluidly connected to the fluid contained in the holding tank, and there is at least one small liquid bead residing in the accessory tube close to the input end, the small liquid bead sealing the tube bore and the head space,
 wherein the tube bore and the headspace are filled with air or inert gas, and dispensing the fluid from the reservoir draws the small liquid bead to move in the tube bore toward the reservoir end, the small liquid bead continuing to seal the tube bore and the headspace.

13. The fluid dispenser of claim 1, wherein the reservoir comprises
 a holding tank integral to the dispenser case, the holding tank containing a plurality of doses of the fluid, there is an outer cover around the dispenser case, the outer cover and the dispenser case enclose a helical vent path, the helical vent path having an outer end and an inner end, the inner end fluidly connected to a headspace in the holding tank, the headspace being fluidly connected to the fluid contained in the holding tank, and there is at least one small liquid bead residing in the helical vent path close to the outer end, the small liquid bead sealing the vent path and the head space,
 wherein the vent path and the headspace are filled with air or inert gas, and dispensing the fluid from the reservoir draws the small liquid bead to move in the vent path toward the inner end, the small liquid bead continuing to seal the vent path and the headspace.

14. The fluid dispenser of claim 1, wherein the reservoir comprises
 a holding tank integral to the dispenser case, the holding tank containing a plurality of doses of the fluid, the dispenser case includes a base, the base entrapping a spiral groove, the spiral groove defining a helical vent path, an outer end and an inner end, the inner end fluidly connected to a headspace in the holding tank, the headspace being fluidly connected to the fluid contained in the holding tank, and there is at least one small liquid bead residing in the spiral vent path close to the outer end, the small liquid bead sealing the vent path and the head space,
 wherein the vent path and the headspace are filled with air or inert gas, and dispensing the fluid from the reservoir draws the small liquid bead to move in the vent path toward the inner end, the small liquid bead continuing to seal the vent path and the headspace.

15. The fluid dispenser of claim 1, further comprising an extended shroud disposed on top of the dispenser case, wherein the fluid dispenser is used to dispense the fluid into an eye positioned in front of the outlet orifice, and the extended shroud prevents the eye seeing the pressing of the push button.

16. The fluid dispenser of claim 1, wherein the actuating assembly comprises a push button having a first spring member attached to a lower part of the push button and further comprising a flip closure positioned on top of the dispenser case,
 wherein the flip closure is capable of being positioned in a upright or downward stance, the fluid dispenser is used to dispense the fluid into an eye positioned in front of the outlet orifice, and the flip closure, when positioned upright, prevents the eye from seeing the pressing of the push button.

17. The fluid dispenser of claim 1, wherein the fluid discharged from the outlet orifice forms a stream, single droplet or collection of droplets that follow an arced gravity-assisted trajectory.

18. The fluid dispenser of claim 1, further comprising an extended outlet attached to the dispenser case, the extended outlet covering and extending the outlet orifice, wherein the fluid is discharged through the extended outlet.

* * * * *